US010188325B2

(12) United States Patent
Esenaliev

(10) Patent No.: US 10,188,325 B2
(45) Date of Patent: *Jan. 29, 2019

(54) WEARABLE, NONINVASIVE GLUCOSE SENSING METHODS AND SYSTEMS

(71) Applicant: Rinat O. Esenaliev, League City, TX (US)

(72) Inventor: Rinat O. Esenaliev, League City, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/953,275

(22) Filed: Nov. 27, 2015

(65) Prior Publication Data

US 2016/0192867 A1    Jul. 7, 2016

Related U.S. Application Data

(63) Continuation-in-part of application No. 13/416,963, filed on Mar. 9, 2012, now Pat. No. 9,167,993.

(60) Provisional application No. 62/085,183, filed on Nov. 26, 2014, provisional application No. 62/085,190, filed on Nov. 26, 2014.

(51) Int. Cl.
*A61B 5/145* (2006.01)
*A61B 8/00* (2006.01)
*A61B 5/00* (2006.01)
*A61B 5/107* (2006.01)
*A61B 8/08* (2006.01)
*A61B 5/1455* (2006.01)
*A61B 8/10* (2006.01)

(52) U.S. Cl.
CPC ........ *A61B 5/14532* (2013.01); *A61B 5/0059* (2013.01); *A61B 5/0095* (2013.01); *A61B 5/1075* (2013.01); *A61B 5/6801* (2013.01); *A61B 8/4227* (2013.01); *A61B 8/5223* (2013.01); *A61B 5/0002* (2013.01); *A61B 5/1455* (2013.01); *A61B 5/681* (2013.01); *A61B 5/6803* (2013.01); *A61B 5/7264* (2013.01); *A61B 5/7445* (2013.01); *A61B 5/7465* (2013.01); *A61B 8/10* (2013.01)

(58) Field of Classification Search
CPC . A61B 5/1455; A61B 5/14532; A61B 5/0095; A61B 8/5223
See application file for complete search history.

(56) References Cited

U.S. PATENT DOCUMENTS 5,119,819 A * 6/1992 Thomas ............ A61B 5/14532
600/347
5,692,504 A * 12/1997 Essenpreis ......... A61B 5/14532
600/316
6,954,662 B2 * 10/2005 Freger ................ A61B 5/14532
600/316

(Continued)

*Primary Examiner* — Eric Winakur
(74) *Attorney, Agent, or Firm* — Robert W Strozier

(57) ABSTRACT

New wearable systems for noninvasive glucose sensing include an ultrasound generator, an ultrasound detector and a feedback unit. Methods for noninvasive glucose sensing using a wearable device include measuring a thickness (geometrical and/or optical) of a target tissue or a time of flight of ultrasound or optical pulses in the target tissue and determining a glucose value from the thickness of the target tissue or the time of flight in the target tissue in accordance with a target tissue thickness (geometrical and/or optical) or time of flight versus glucose calibration curve.

24 Claims, 20 Drawing Sheets

(56) References Cited

U.S. PATENT DOCUMENTS

2007/0255141 A1* 11/2007 Esenaliev .......... A61B 5/14532
600/316

* cited by examiner

WEARABLE, NONINVASIVE GLUCOSE SENSING METHODS AND SYSTEMS

RELATED APPLICATION

This application is a continuation-in-part of U.S. patent application Ser. No. 13/416,963 filed Mar. 9, 2012, now U.S. Pat. No. 9,167,993 issued 27 Oct. 2015.

BACKGROUND OF THE INVENTION

1. Field of the Invention

The present invention relates to a method for noninvasive glucose sensing and a system for implementing the method and to methods for noninvasive glucose sensing with wearable devices and systems for implementing the methods.

More particularly, the present invention relates to a method for noninvasive glucose sensing including the step of measuring a thickness of a target tissue or a time of flight of ultrasound or optical pulses in the target tissue and determining a glucose value from the thickness of the target tissue or the time of flight in the target tissue in accordance with a target tissue thickness or time of flight versus glucose calibration curve and a system for implementing the method. The present invention also relates to a method for noninvasive glucose sensing using a wearable device and including the step of measuring a thickness of a target tissue or a time of flight of ultrasound or optical pulses in the target tissue and determining a glucose value from the thickness of the target tissue or the time of flight in the target tissue in accordance with a target tissue thickness or time of flight versus glucose calibration value or glucose calibration curve and a system for implementing the method.

2. Description of the Related Art

Other techniques can be used for tissue dimension measurement. Near infrared absorption spectroscopy can provide tissue thickness measurement (U.S. Pat. No. 6,671, 542). However, techniques with higher resolution are needed for accurate glucose monitoring. One can use optical refractometry (U.S. Pat. No. 6,442,410) for noninvasive blood glucose measurement. However, this technique has limitations associated with low accuracy and specificity of glucose monitoring.

Other systems based on other techniques can be potentially wearable and can be used for tissue dimension measurement. Near infrared absorption spectroscopy can provide tissue thickness measurement (U.S. Pat. No. 6,671, 542). However, techniques with higher resolution are needed for accurate glucose monitoring. One can use optical refractometry (U.S. Pat. No. 6,442,410) for noninvasive blood glucose measurement. However, this technique has limitations associated with low accuracy and specificity of glucose monitoring.

U.S. Pat. No. 7,039,446 B2 discloses a variety of techniques for analyte measurements but does not disclose how to measure tissue thickness and use the thickness measurements for glucose concentration monitoring. Acoustic velocity measurement in blood was proposed in U.S. Pat. No. 5,119,819 for glucose monitoring. However, tissue thickness measurements were not disclosed. Photoacoustic techniques were proposed in U.S. Pat. No. 6,846,288 B2 for measurement of blood glucose concentration by generating photoacoustic waves in blood vessels.

Most of the approaches proposed for noninvasive glucose monitoring are based on near infrared spectroscopy, Raman spectroscopy, polarimetry, and electro-impedance technique. Low glucose-induced signal and insufficient specificity and accuracy are major limitations of these approaches. Development of a noninvasive glucose monitor remains one of the most challenging (and important) biomedical problems.

These and other techniques proposed for noninvasive glucose monitoring have limited accuracy and specificity. These and other systems proposed for noninvasive glucose monitoring have limited accuracy and specificity. Moreover, the systems based on these techniques are bulky, heavy, expensive, and impractical for use as wearable devices.

Thus, there is still a need in the art for simple noninvasive glucose sensing methods and systems. Thus, there is still a need in the art for noninvasive glucose sensing methods and systems that are wearable, have acceptable size, weight, price, and are practical for use.

SUMMARY OF THE INVENTION

The present invention provides a blood glucose monitoring technique that is critically important for diabetic patients. Tight glucose control decreases dramatically complications and mortality associated with diabetes. Blood glucose monitoring is an important part of blood glucose control. At present, standard techniques for blood glucose monitoring are invasive and require a drop of blood or interstitial fluid for measurement. Continuous glucose monitoring (CGM) systems developed for diabetics require insertion of a sensor in skin and are not free of limitations.

The present invention also provides a noninvasive blood glucose monitoring technique that would also be invaluable in critically ill patients, regardless of whether those patients are diabetic. Clinical studies clearly establish that morbidity and mortality are reduced in patients requiring intensive care if blood glucose is tightly controlled between 80 and 110 mg/dL (Van den Berghe G, 2005; Vanhorebeek I, 2005; van den Berghe G, 2001). However, conventional techniques for tightly controlling blood glucose have several limitations, including the need for frequent blood sampling and the risk that insulin administration will induce hypoglycemia (blood glucose <60 mg/dL) between sampling intervals and that hypoglycemia therefore will not be promptly diagnosed and treated. A continuous method of monitoring blood glucose by measuring tissue thickness would greatly improve the ease and safety of tightly controlling blood glucose with insulin in critically ill patients.

The measurement of dimensions or time of flight can be performed in a variety of tissues including, but not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue. The dimension(s) of these tissues can change with blood glucose concentration. For instance, our studies demonstrated that increase of blood glucose concentration may decrease the thickness (and optical thickness) of and time of flight of ultrasound pulses in the skin tissues (namely, dermis). Measurements of dimensions of specific tissue layers (within one of these tissues) can be used for glucose monitoring. Measurement of one, two or more dimensions can be performed for more accurate, specific, and sensitive glucose monitoring. Ratios of dimensions of two or more tissues can be used for more robust, accurate, specific, and sensitive glucose monitoring. For instance, increasing blood glucose concentration may increase lens thickness and decrease anterior chamber thickness. The ratio of these changes may provide robust, accurate, and sensitive blood glucose monitoring. One can use measurement of total dimensions of complex tissues consisting of two or more different tissues. Measurement of time of flight of ultrasound or optical waves in these tissues, or optical thickness of these tissues can also be used for non-invasive glucose monitoring without calculating or determining geometrical thickness or other dimensions of these tissues.

Wearable Devices

The present invention provides a wearable, noninvasive, and continuous glucose monitoring technique that is critically important for diabetic patients. Tight glucose control decreases dramatically complications and mortality associated with diabetes. Blood glucose monitoring is an important part of blood glucose control. At present, standard techniques for blood glucose monitoring are invasive and require a drop of blood or interstitial fluid for measurement. Continuous glucose monitoring (CGM) systems developed for diabetics require insertion of a sensor in skin and are not free of limitations associated with tissue trauma and inflammation, immune response, and encapsulation of the sensing area by proteins. A wearable, noninvasive, continuous glucose monitor would considerably improve the quality of life for diabetic patients, improve their compliance with glucose monitoring, and reduce complications associated with the disease.

The present invention provides a blood glucose monitoring technique that is critically important for diabetic patients. Tight glucose control decreases dramatically complications and mortality associated with diabetes. Blood glucose monitoring is an important part of blood glucose control. At present, all techniques for blood glucose monitoring are invasive and require a drop of blood or interstitial fluid for measurement. These techniques cannot provide continuous data. Recently, insertable continuous glucose sensors were developed, but they require insertion of a glucose sensing probe in the skin or subcutaneous tissue, produce trauma to tissue, and have limitations associated with body response to trauma, frequent recalibration, and low accuracy due to the body response and due to interference from substances such as acetaminophen and others.

The measurement of dimensions or time of flight can be performed using a wearable device in a variety of tissues including, but not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue. The dimension(s) of these tissues can change with blood glucose concentration. For instance, our studies demonstrated that increase of blood glucose concentration may decrease the thickness (and optical thickness) of and time of flight of ultrasound pulses in the skin tissues (namely, dermis). Measurements of dimensions of specific tissue layers (within one of these tissues) can be used for glucose monitoring. Measurement of one, two or more dimensions can be performed for more accurate, specific, and sensitive glucose monitoring. Ratios of dimensions of two or more tissues can be used for more robust, accurate, specific, and sensitive glucose monitoring. For instance, increasing blood glucose concentration may increase lens thickness and decrease anterior chamber thickness. The ratio of these changes may provide robust, accurate, and sensitive blood glucose monitoring. One may use measurement of total dimensions of complex tissues consisting of two or more different tissues. Measurement of time of flight of ultrasound or optical waves in these tissues, or optical thickness of these tissues can also be used for non-invasive glucose monitoring without calculating or determining geometrical thickness or other dimensions of these tissues.

BRIEF DESCRIPTION OF THE DRAWINGS

The invention can be better understood with reference to the following detailed description together with the appended illustrative drawings in which like elements are numbered the same.

A short radiofrequency (typically nanosecond) pulse can be used instead of the optical pulse to generate the ultrasound waves.

Figure 11:
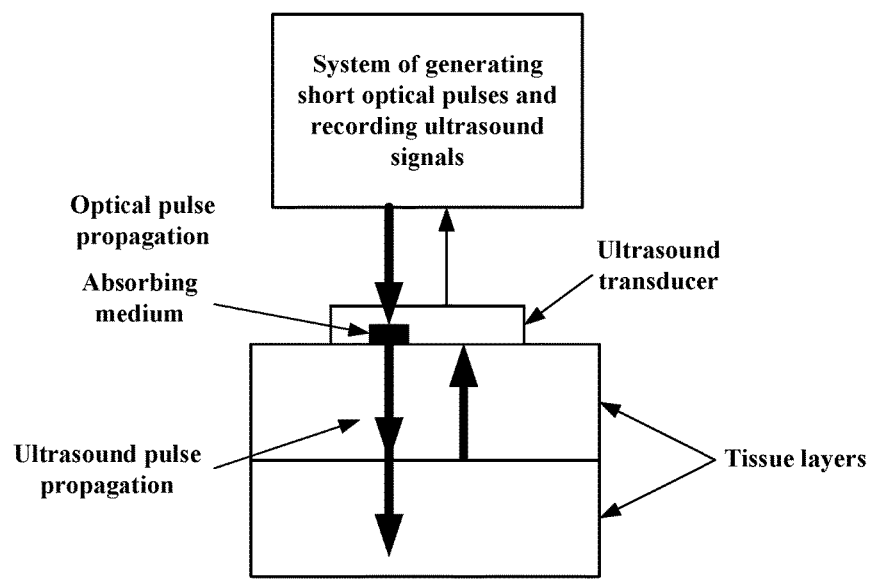

FIG. 11 depicts an optical system for generating short, broad-band ultrasound pulses in an optically absorbing medium. The medium is attached to the tissue surface. The optical system produces at least one short (typically nanosecond or picosecond) optical pulse and directs it on the absorbing medium. The energy of the optical pulse is absorbed by the medium that results in generation of a short ultrasound (acoustic) pulse. The ultrasound pulse then propagates in the tissue and is reflected from tissue layers. An ultrasound transducer detects the reflected ultrasound pulses and a processor analyzes the signal from the transducer and calculates the time of flight of the ultrasound pulses and glucose concentration. A short (typically nanosecond) radiofrequency electromagnetic pulse can be used instead of the short optical pulse to generate a short, broadband ultrasound pulse in a radiofrequency absorbing medium.

Figure 12A:
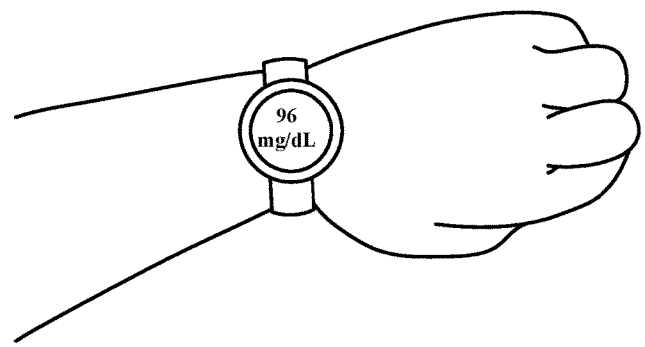

FIG. 12A depicts an embodiment of a wearable, noninvasive glucose monitoring system—a wrist watch.

Figure 12B:
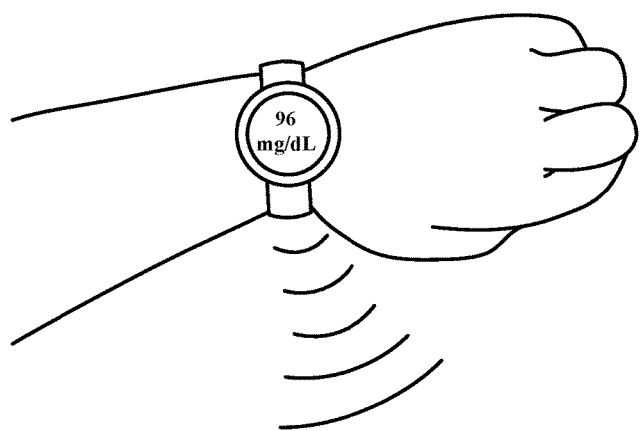
Figure 12B:
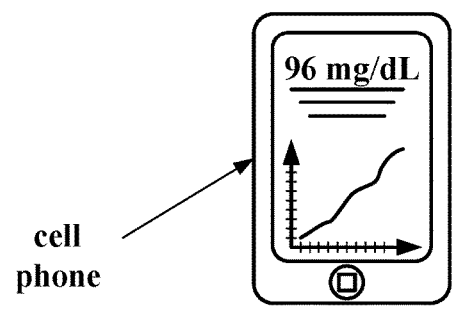

FIG. 12B depicts another embodiment of a wearable, noninvasive glucose monitoring system—a wrist watch.

Figure 13:
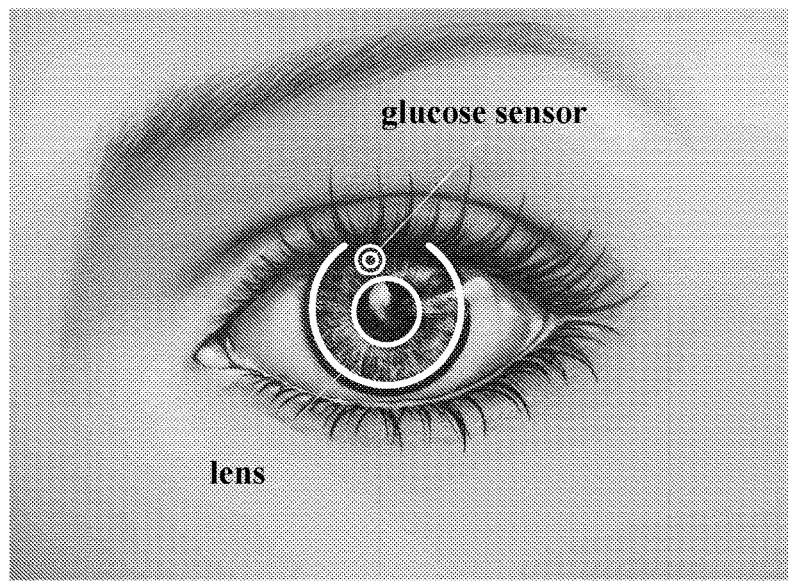

FIG. 13 depicts an embodiment of a wearable, noninvasive glucose monitoring system—contact lens.

Figure 14:
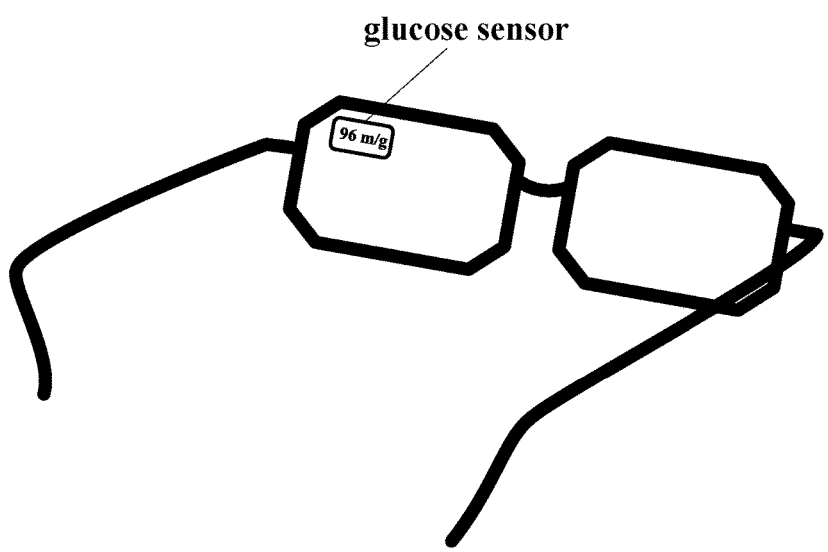

FIG. 14 depicts an embodiment of a wearable, noninvasive glucose monitoring system—glasses.

Figure 15:
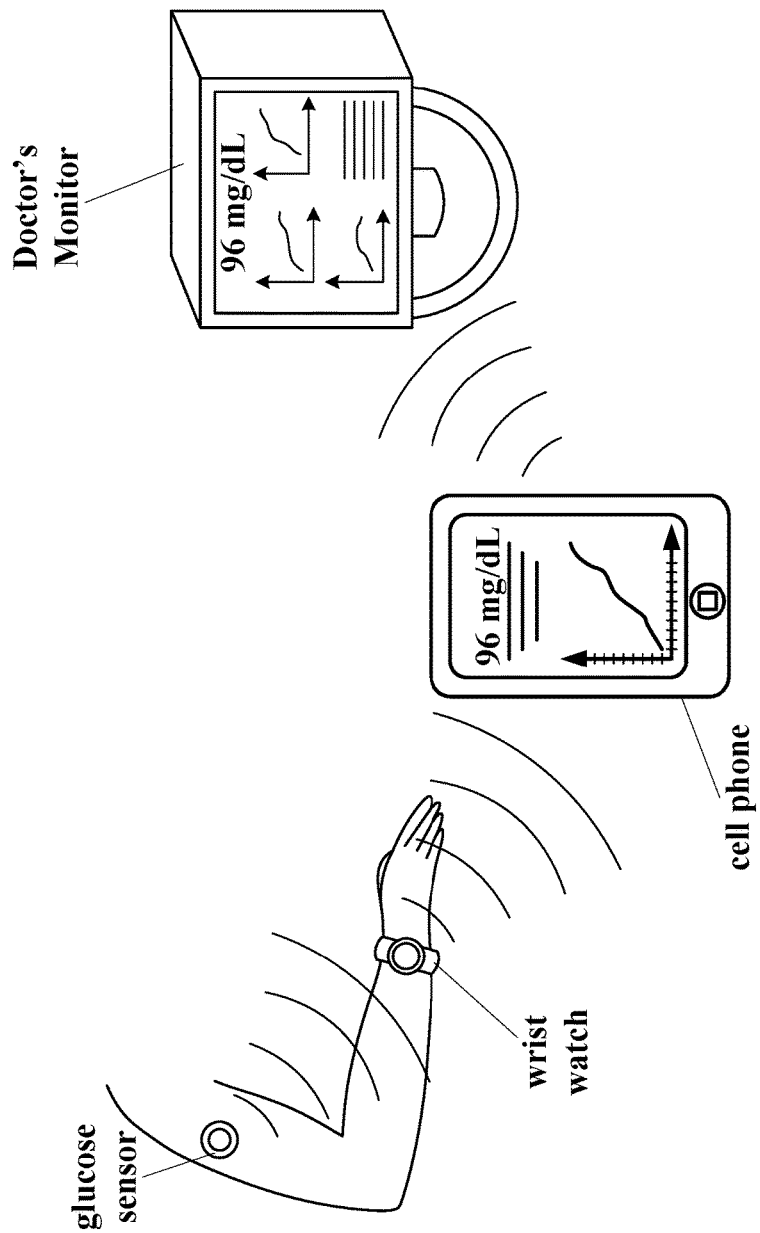

FIG. 15 depicts another embodiment of a wearable, noninvasive glucose monitoring system—a wrist watch.

Figure 16:
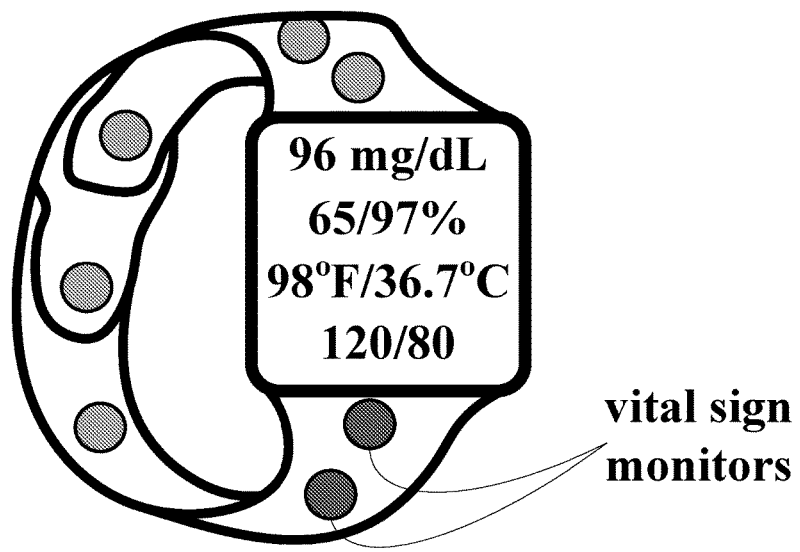

FIG. 16 depicts another embodiment of a wearable, noninvasive glucose monitoring system—a wrist watch.

Figure 17:
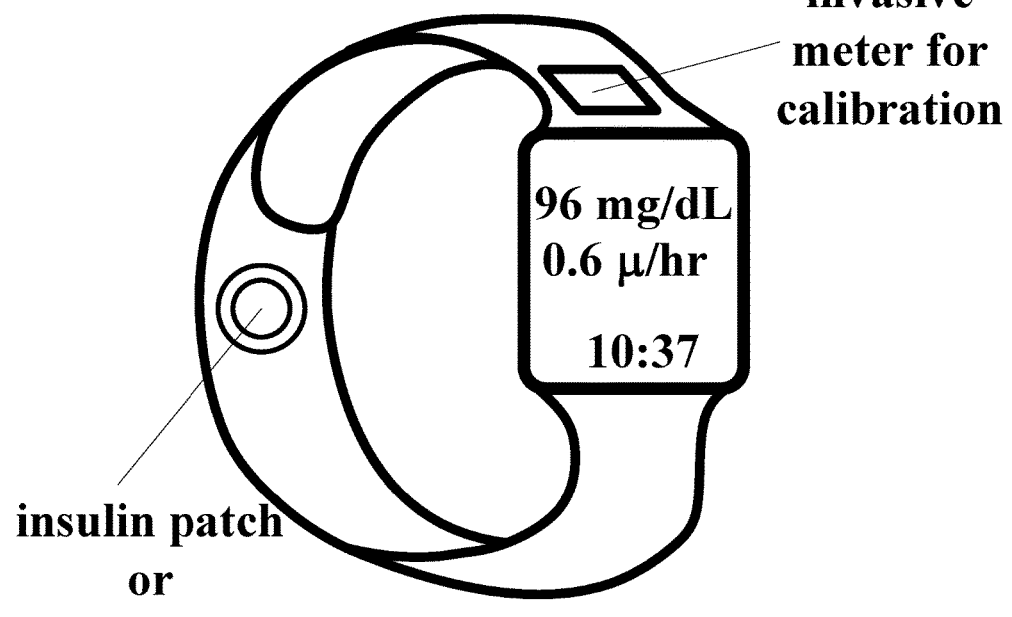

FIG. 17 depicts another embodiment of a wearable, noninvasive glucose monitoring system—a wrist watch.

Figure 18:
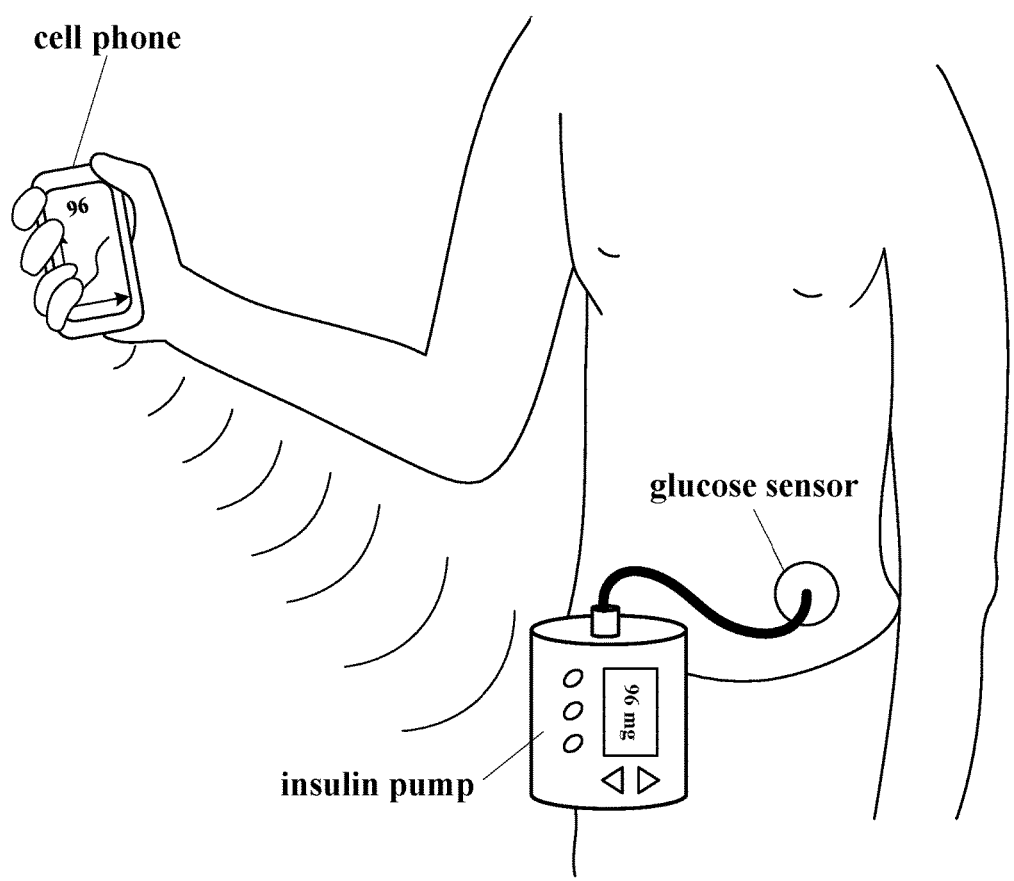

FIG. 18 depicts another embodiment of a wearable, noninvasive glucose monitoring system—stomach patch.

DETAILED DESCRIPTION OF THE INVENTION

The invention discloses method and apparatus for noninvasive glucose monitoring and sensing with electromagnetic (including optical) waves or ultrasound. This method is based on absolute or relative measurement of tissue dimensions (or changes in the dimensions) including, but not limited to: thickness, length, width, diameter, curvature, roughness as well as optical thickness and time of flight of optical or ultrasound pulses. Changes in blood glucose concentration may increase or decrease tissue dimensions due to a variety of possible mechanisms. One of them is the glucose-induced osmotic effect. The osmotic effect may decrease or increase tissue dimension(s) depending on tissue type, structure, location, condition, cell density, blood content, and vascularization. By measuring noninvasively absolute or relative changes in at least one dimension of at least one tissue or tissue layer, one can monitor blood glucose concentration noninvasively. Variation of glucose concentration may also change sound velocity and refractive index. Thus, the measurement of time of flight of the ultrasound or optical pulses may provide more robust, accurate, and specific monitoring of blood glucose concentration compared to geometrical dimension measurements.

Tissues include, but are not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue. The dimension(s) of these tissues can change with blood glucose concentration. For instance, our studies demonstrated that increase of blood glucose concentration may decrease the time of flight in and thickness of the skin tissues (namely, dermis). Measurements of dimensions of specific tissue layers (within one of these tissues) can be used for glucose monitoring. Measurement of one, two or more dimensions can be performed for more accurate, specific, and sensitive glucose monitoring. Ratio of dimensions of two or more tissues can be used for more robust, accurate, specific, and sensitive glucose monitoring. For instance, increase of blood glucose concentration may increase lens thickness and decrease anterior chamber thickness (Furushima et al., 1999). The ratio of these changes may provide robust, accurate, and sensitive blood glucose monitoring. One can use measurement of total dimensions of complex tissues consisting on two or more different tissues. Measurement of optical thickness of these tissues can also be used for non-invasive glucose monitoring.

The electromagnetic wave or ultrasound with at least one wavelength (frequency) is directed to the tissue or tissue layer. Reflected, refracted, transmitted, scattered, backscattered, or forward-scattered waves can be used for measurement of the tissue dimensions. The measurements of tissue dimensions may be performed in the reflection mode or in the transmission mode. In the reflection mode, irradiation and detection are performed from one side. In the transmission mode, irradiation and detection are performed from different sides.

The electromagnetic waves include optical radiation (near infrared, infrared, far infrared, visible, and UV light in the wavelength range from about 200 nanometers to about 100 microns), terahertz waves, microwaves, radiowaves, low-frequency waves, static electric or magnetic filed. A combination of different waves can be used with one, two, or multiple wavelengths (frequencies) can be used for more accurate, specific, and sensitive glucose monitoring.

Ultrasound includes ultrasonic waves in the frequency range from about 20 kHz to about 10 gigahertz. One, two, or multiple frequencies or broad-band ultrasound pulses can be used for more accurate, specific, and sensitive glucose monitoring. The broad-band ultrasound pulses can be generated by using short electromagnetic pulses irradiating a strongly absorbing medium attached to the tissue. Short optical pulses induced by laser and non-laser sources can be used for generation of the broad-band ultrasound pulses.

Combination of electromagnetic waves and ultrasound may provide higher accuracy and specificity of glucose monitoring. Hybrid techniques such as optoacoustics and thermoacoustics can be used for tissue dimension or time of flight measurement. Short optical pulses from laser or non-laser sources or short radiofrequency pulses can be used for generating acoustic waves in the tissue. Acoustic (ultrasound) detectors, preferably, broad-band detectors can be used for detection of the acoustic waves. The time of flight (and glucose-induced signal shift) can be measured by analyzing the optoacoustic and thermoacoustic waves. One can calculate tissue thickness, L, by using the formula: $L=ct$, where c is the speed of sound in tissue. In contrast to the formula presented above for the pure ultrasound technique, the factor of ½ is not used because the optoacoustic or thermoacoustic waves propagate only one way (from tissue to detector). For additional information on optoacoustics the reader is referred to U.S. Pat. Nos. 6,751,490, and 6,498,942, incorporated herein by reference.

The electromagnetic waves and ultrasound can be pulsed, continuous wave, or modulated. Amplitude and/or frequency can be modulated to provide high signal-to-noise ratio.

The measurements can be performed with one or more (array) of detectors of electromagnetic or ultrasound waves. One can use multiple sources of electromagnetic waves or ultrasound for glucose monitoring.

Combination of these techniques with other techniques may provide more accurate, specific, and sensitive glucose monitoring.

The glucose sensing device can be wearable to provide continuous monitoring. A wearable device (like a wrist watch) can be used for continuous skin thickness measurement. One can use specially-designed glasses for glucose monitoring systems based on eye tissue thickness (or optical thickness) or time of flight measurement.

The glucose-sensing probe(s) attached to the tissue can be controlled by a radiofrequency controller remotely to minimize patient's discomfort. Light-weight probes can be used to decrease pressure applied by the probe on the tissue surface and improve accuracy of glucose monitoring.

The tissue temperature may be stabilized and be, preferably, in the range from about 37° C. to about 40° C. A temperature controller with a heater should be used to provide a stable temperature in this range. The stable temperature yields constant speed of sound and refractive index, and therefore, more accurate and specific glucose monitoring. Moreover, tissue warming to these temperatures improves blood flow and glucose transport in the tissues that yield to more accurate and specific glucose monitoring.

General Information

The inventor discloses monitoring blood glucose concentration noninvasively by measuring absolute or relative tissue dimensions (or changes in the dimensions) including, but not limited to: thickness (or optical thickness), length, width, diameter, curvature, roughness as well as time of flight of ultrasound and electromagnetic pulses and optical thickness. The inventor discloses the use of electromagnetic or ultrasound techniques for tissue dimension measurement and, in particular, time of flight techniques based on generation of short and ultrashort ultrasound or electromagnetic pulses, focused light reflection technique and focus-detection technique for noninvasive measurement of tissue thickness as well as other techniques based on detection of reflected, refracted, transmitted, scattered, backscattered, or forward-scattered wave. The inventor has demonstrated in vivo that time of flight of ultrasound pulses in skin and skin thickness decrease with blood glucose concentration. The inventor discloses the use of measurement of time of flight and dimensions of skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue for noninvasive glucose monitoring. The inventor discloses the use of optoacoustic and thermoacoustic techniques for tissue time of flight and dimension measurements. The inventor discloses the use of time of flight changes (signal shift) and ratio of dimensions (or changes in dimensions) of different tissues for more accurate glucose monitoring. The inventor discloses the use of two or more wavelengths (frequencies) for more accurate glucose monitoring. The inventor discloses the use of broad-band ultrasound pulses generated by optical pulses in optically-absorbing media or generated by radiofrequency pulses in radiofrequency absorbing media. The inventor discloses the use of time-resolved techniques based on reflection of ultrashort optical pulses from tissue layers and interfaces. The inventor discloses the use of low-coherence interferometry for geometrical and/or optical thickness measurements. The inventor also discloses the use of this technique for noninvasive blood glucose monitoring in critically ill patients, regardless of whether those patients are diabetic. Clinical studies clearly establish that morbidity and mortality is reduced in patients requiring intensive care if blood glucose is tightly controlled between 80 and 110 mg/dL (Van den Berghe G, 2005; Vanhorebeek I, 2005; van den Berghe G, 2001). However, conventional techniques for tightly controlling blood glucose have several limitations, including the need for frequent blood sampling and the risk that insulin will induce hypoglycemia between sampling intervals and that hypoglycemia will not be promptly diagnosed and treated. A continuous method of monitoring blood glucose by measuring skin thickness or time of flight would greatly improve the ease and safety of tightly controlling blood glucose with insulin therapy in critically ill patients.

The inventor also discloses the use of combined measurement of time of flight of ultrasound or optical pulses with measurement of attenuation, phase, and frequency spectrum of the ultrasound or optical pulses reflected from the tissues to improve accuracy and specificity of glucose monitoring. The attenuation can be measured by analyzing the amplitude of the reflected pulses. The phase and the frequency spectrum can be measured by analyzing the temporal characteristics of the reflected pulses. The amplitude (attenuation), phase, and frequency of the reflected pulses may vary with glucose concentration. Measurement of these parameters or glucose-induced changes in these parameters may provide additional information which combined with the time of flight measurements can be used for more accurate and specific glucose monitoring.

Blood glucose monitoring is critically important for diabetic patients. Tight glucose control decreases dramatically complications and mortality associated with diabetes. Blood glucose monitoring is an important part of blood glucose control. At present, all techniques for blood glucose monitoring are invasive and require a drop of blood or interstitial fluid for measurement.

There are no techniques for noninvasive glucose monitoring on the market. The disclosed technique is novel because glucose-induced changes in tissue geometrical and/or optical dimensions or time of flight have not been studied yet. This invention is not obvious to a person having ordinary skill in the art to which this invention pertains. It is necessary to understand and demonstrate why and how changes in blood glucose concentration decrease or increase tissue geometrical and or optical dimensions or time of flight of ultrasound or optical pulses.

The broadest application is noninvasive blood glucose monitoring in diabetic patients. However, continuous monitoring of blood glucose in critically ill patients would contribute a separate, clinically invaluable tool in patients who are not diabetic.

The noninvasive glucose monitoring of this invention can be performed by using a variety of techniques. The following examples are shown to demonstrate possible approaches to glucose monitoring by using dimension or time of flight measurements with different techniques in various tissues.

Figure 1A:
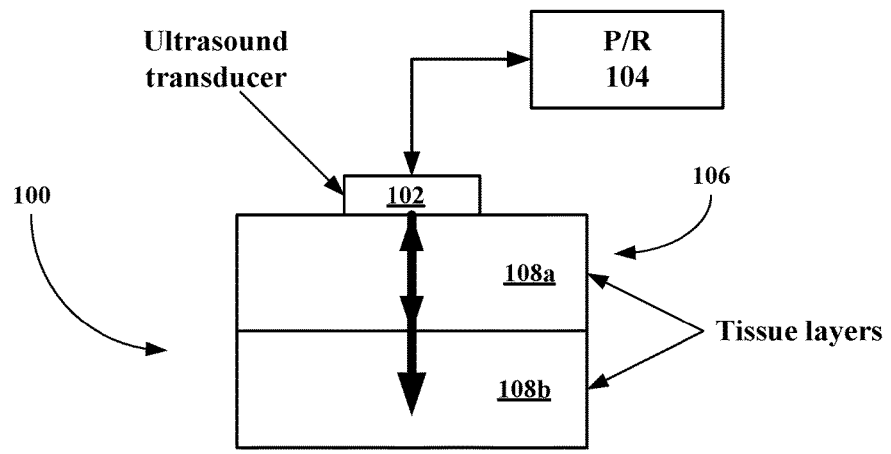
FIG. 1A depicts an embodiment of an ultrasound system for tissue thickness or ultrasound time of flight measurement.

Referring now to FIG. 1A, an embodiment of a system of this invention, generally 100, is shown to include an ultrasound transducer 102 in electrical communication or connected electronically or electrically to a pulser/receiver (P/R) 104. The P/R 104 generates at least one electrical pulse which is converted into an ultrasound pulse by the transducer 102. The ultrasound pulse propagates in a tissue 106 and is reflected from tissue layers 108a&b due to an acoustic impedance difference (mismatch) between the layers 108a&b. The reflected ultrasound pulses are detected by the transducer 102 and analyzed by the P/R 104 to calculate the time of flight or thickness of the layers 108a&b. The time of flight or thickness (or their changes) is then converted into glucose concentration or changes in glucose concentration by using a processor and glucose concentration is displayed by a display. The processor and display can be incorporated in the pulser/receiver in one casing or connected to the pulser/receiver using wires or using wireless radiofrequency communication.

Figure 1B:
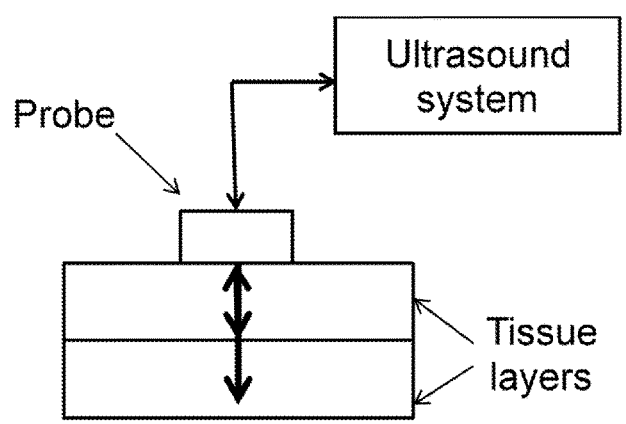
FIG. 1B depicts an embodiment of a compact ultrasound system GWA for tissue thickness or ultrasound time of flight measurement. A highly compact version GWR of the system has cell phone size, is wearable, and can be calibrated to provide noninvasive glucose concentration (both current and continuous glucose concentrations).

Referring now to FIG. 1B, an embodiment of this invention, a compact ultrasound system GWA is connected to the probe and generates electrical pulse. The probe converts the electrical pulse into ultrasound wave (pulse) and directs it to skin. The ultrasound pulse propagates in the skin and reflects from tissue layers. Probe detects the reflected pulses and converts them into electrical pulses. The system measures the changes in ultrasound time of flight (i.e., the system measures ultrasound signal shift). Specially developed algorithms and software process the data and the system displays current and continuous glucose concentration.

Figure 2:
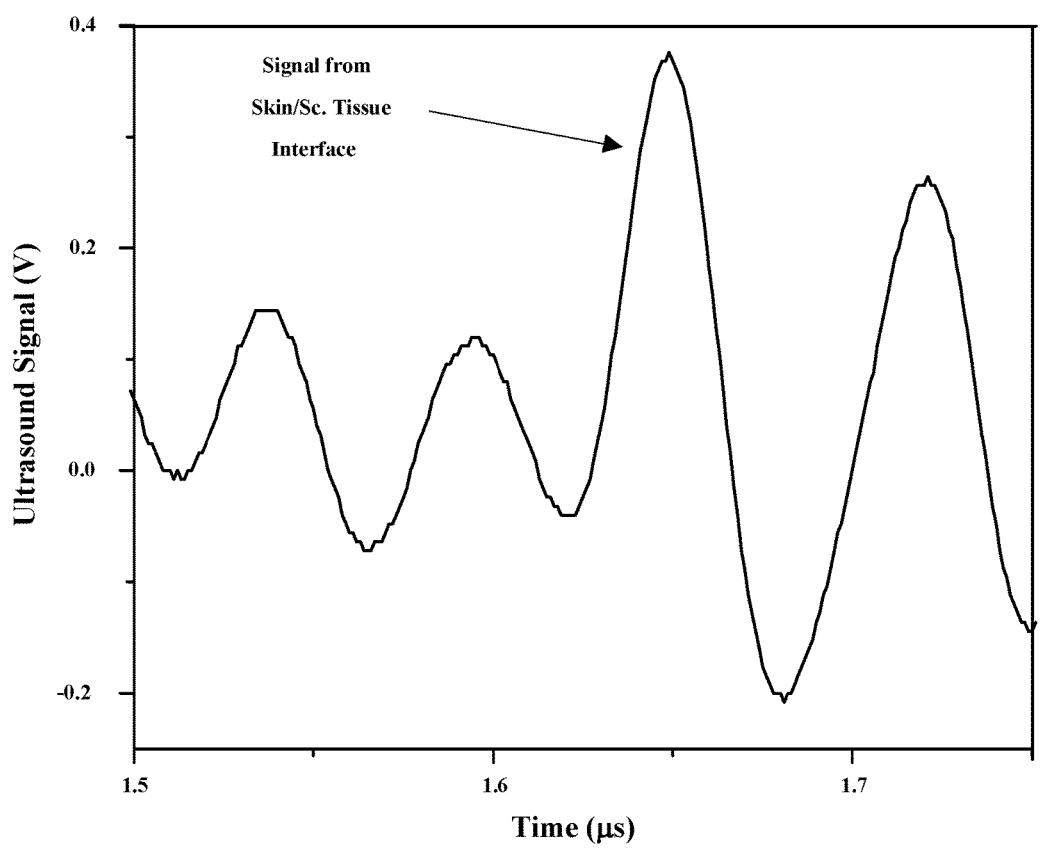
FIG. 2 depicts a typical ultrasound signal from the skin/subcutaneous tissue interface from a human subject (forearm area) recorded by the system of this invention as shown in FIG. 1A.

Referring now to FIG. 2, a 20-MHz non-focused piezoelectric transducer was used to generate short ultrasound pulses. The signal is resulted from acoustic impedance mismatch between the skin and subcutaneous tissue. The time of flight of the ultrasound pulses from the upper skin surface to the skin/subcutaneous tissue interface and back, t, is equal to 1.65 mks (microseconds). This time of flight varies with glucose concentration. Glucose-induced changes in skin result in temporal shift of the signal Δt, due to the changes in the time of flight. By measuring the signal shift one can monitor glucose concentration. This can be done without calculating the geometrical thickness of the skin (or any other tissue). Thus, the system can monitor glucose concentration by measuring the time of flight of the ultrasound pulses (waves) t or changes in the time of light Δt. One can calculate skin thickness, L, by using the formula: L=ct/2, where c is the speed of sound in skin and factor of ½ is due to the propagation of the ultrasound pulse from the skin surface to the interface and back. The skin thickness measured with this system is equal to L=1.5 mm/mks×1.65 ms/2=1.24 mm assuming that c=1.5 mm/mks (typical speed of sound in soft tissues).

Figure 3A:
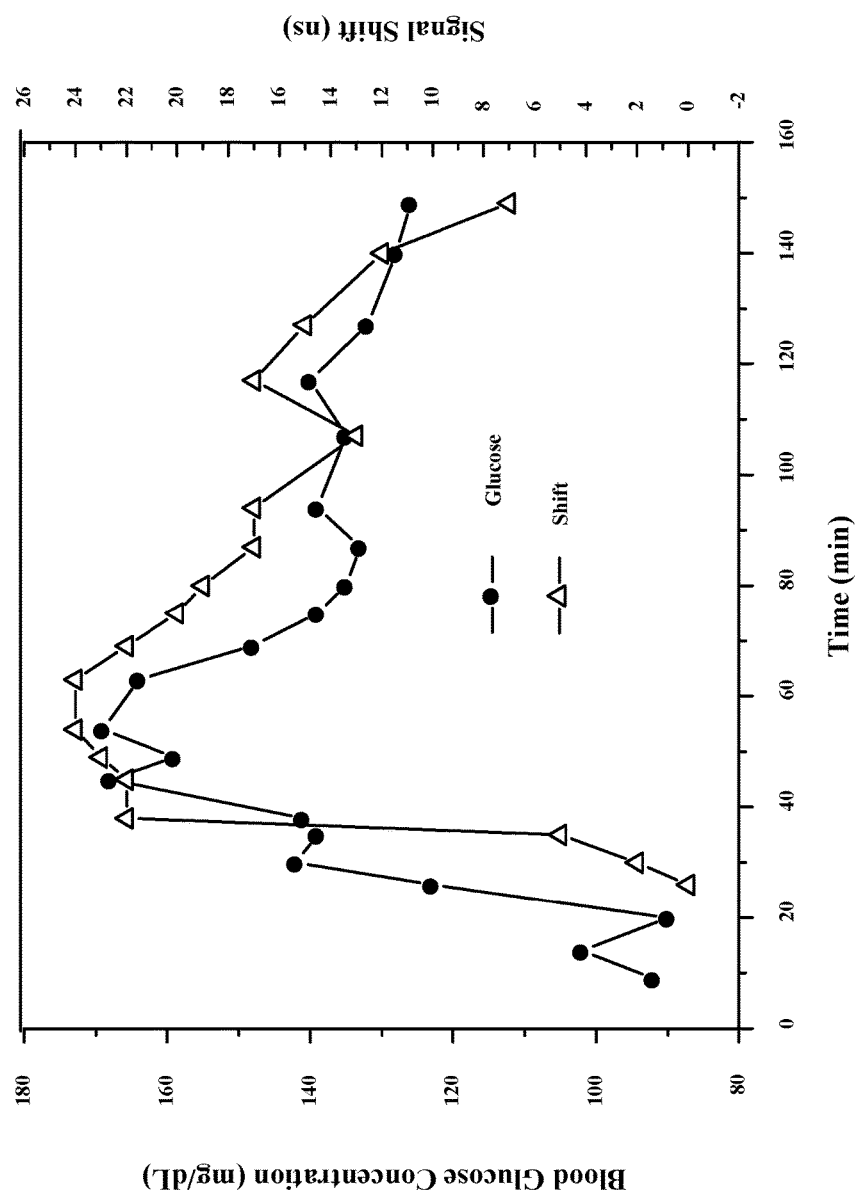
FIG. 3A shows blood glucose concentration (solid circles) in a human subject before and after a sugar drink at the $20^{th}$ minute (76 g of sugar in 650 mL of water).

Referring now to FIG. 3A, blood glucose concentration was measured with a standard invasive technique involving blood sampling from finger tips with a lancet. The ultrasound system shown in FIG. 1A was used to measure time of flight of ultrasound waves in skin t and changes in the time of flight Δt (the signal shift). The transducer was attached to the subject's forearm and detected continuously the ultrasound pulses reflected from the skin. The shift of the signals recorded at the time of blood sampling (and, therefore, the time of flight of ultrasound pulses in the skin) closely follows blood glucose concentration. The time of flight decreased with increase of blood glucose concentration. The positive signal shift plotted in the graph corresponds to decrease of the time of flight, while negative values of the signal shift correspond to increase of the time of flight.

Figure 3B:
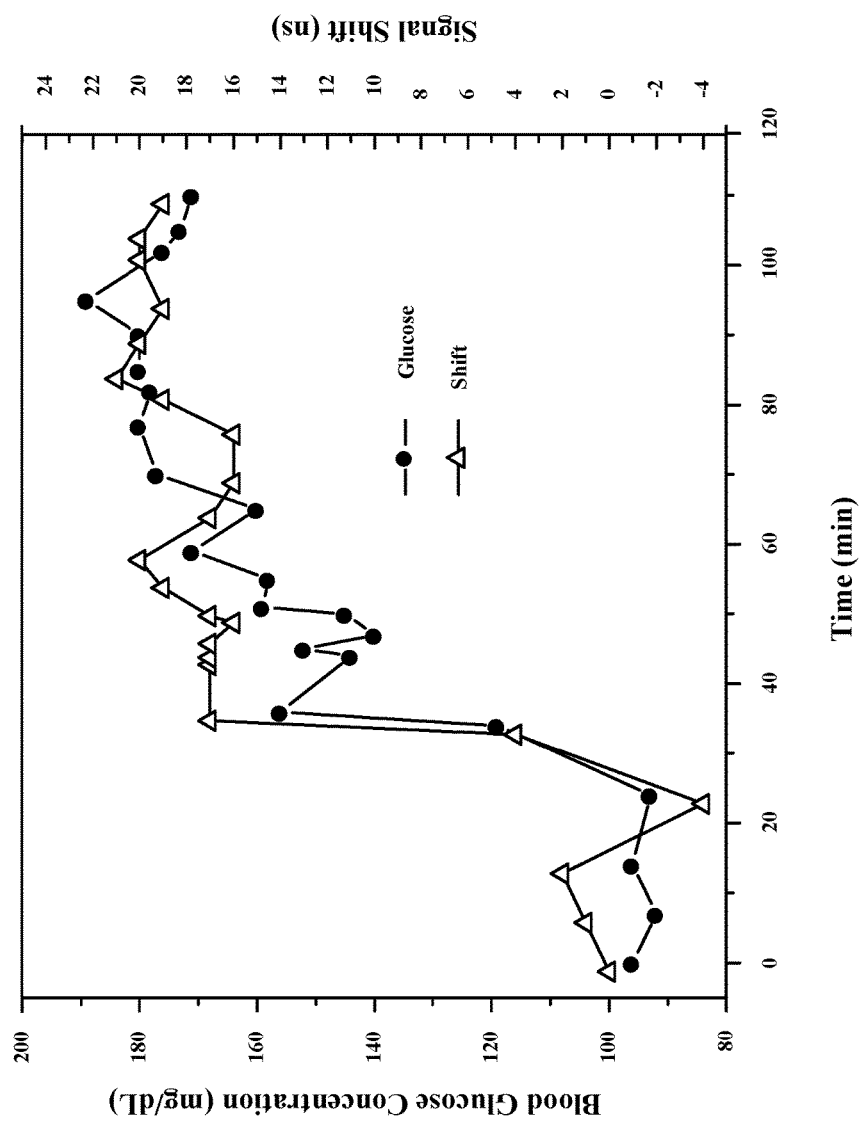
FIG. 3B depicts similar in vivo results before and after a higher glucose load (108 g of sugar in 1 L of water) at $25^{th}$ minute. The measurements were performed with the same ultrasound system from the subject's forearm. The data show good correlation of the signal shift (and, therefore, time of flight of ultrasound pulses in the skin) with blood glucose concentration.

Referring now to FIG. 3B, blood glucose concentration was measured with the same ultrasound system in a human subject before and after a higher glucose load (108 g of sugar in 1 L of water) at $25^{th}$ minute. The ultrasound measurements were performed from the subject's forearm. The data show good correlation of the signal shift (and, therefore, time of flight of ultrasound pulses in the skin) with blood glucose concentration.

Figure 3C:
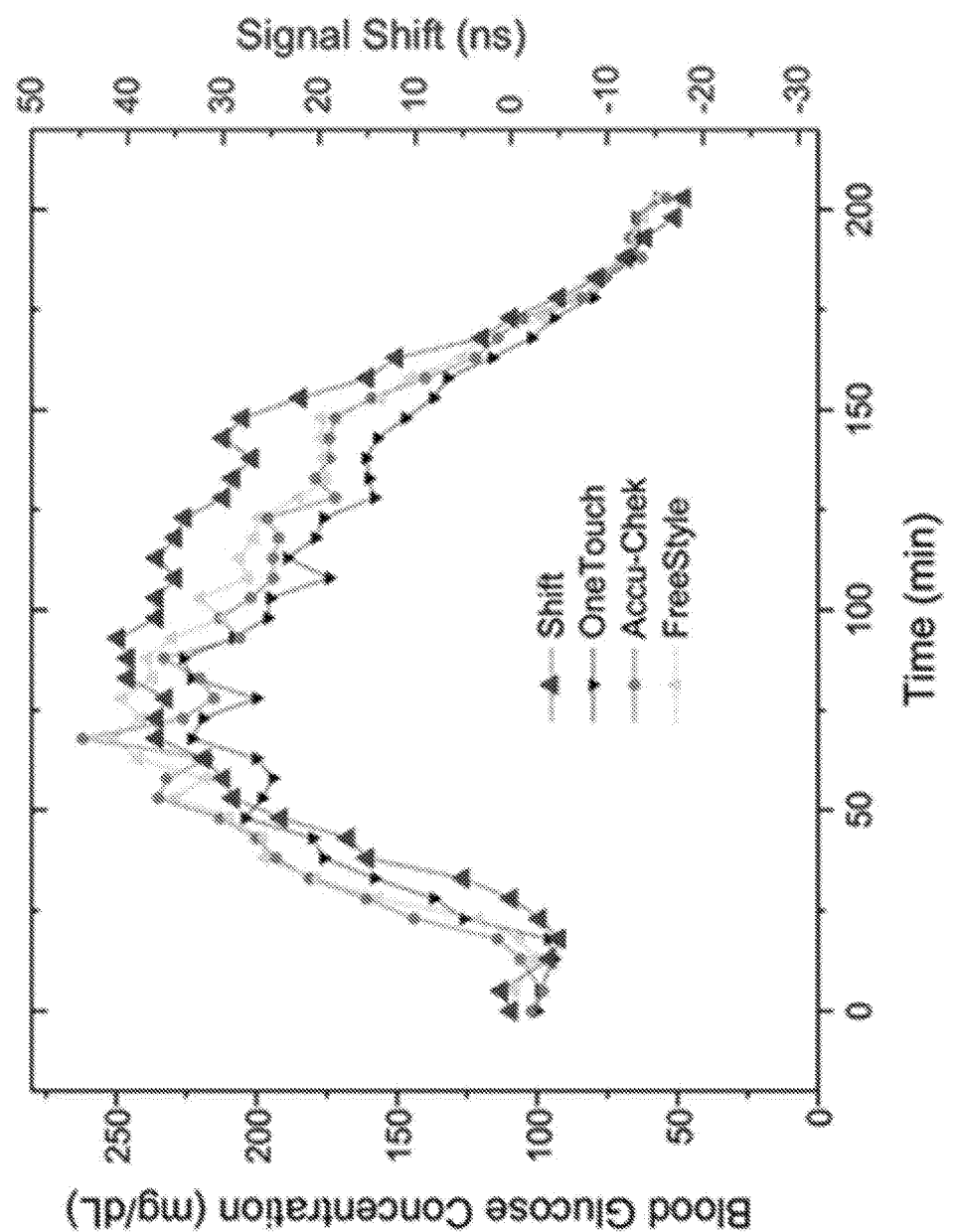
FIG. 3C shows signal shift measured with the compact ultrasound system GWA and blood glucose concentration obtained from a non-diabetic subject. Blood glucose concentration was measured with three glucose meters (OneTouch Ultra 2, Accu-Check, and FreeStyle).

Referring now to FIGS. 3C-F the signal shift (the changes in time of flight) were measured with the compact ultrasound system GWA shown in FIG. 1B. FIG. 3C shows the signal shift and blood glucose concentration obtained from a non-diabetic subject. After the baseline measurements for first 10 minutes the subject had a 100 g glucose drink Blood glucose concentration was measured with three glucose meters (OneTouch Ultra 2, LifeScan, Inc.; Accu-Check Aviva Plus, Roche Diagnostics; and FreeStyle Lite, Abbott Diabetes Care, Inc.). The decrease in time of flight (presented as a positive signal shift) closely followed the increase in blood glucose concentration. Then both blood glucose concentration and signals shift decreased.

Figure 3D:
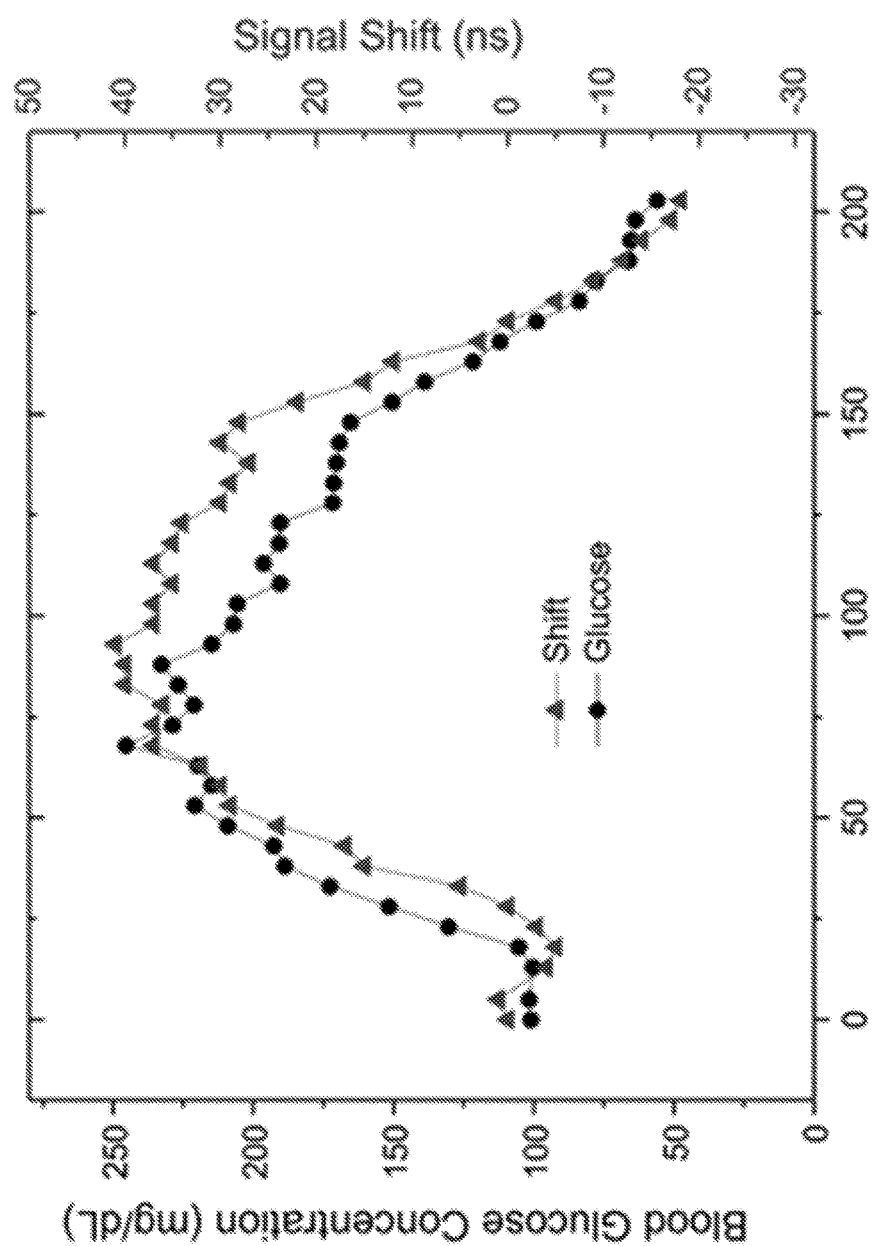
FIG. 3D shows signal shift measured with ultrasound system GWA and blood glucose concentration averaged for the three glucose meters.

FIG. 3D shows the signal shift measured with ultrasound system GWA and blood glucose concentration averaged for the three glucose meters to provide higher accuracy of the invasive glucose concentration measurements. The signal shift followed blood glucose concentration in the whole range from 56 to 230 mg/dL which includes the hypo-, normo-, and hyperglycemic concentrations.

Figure 3E:
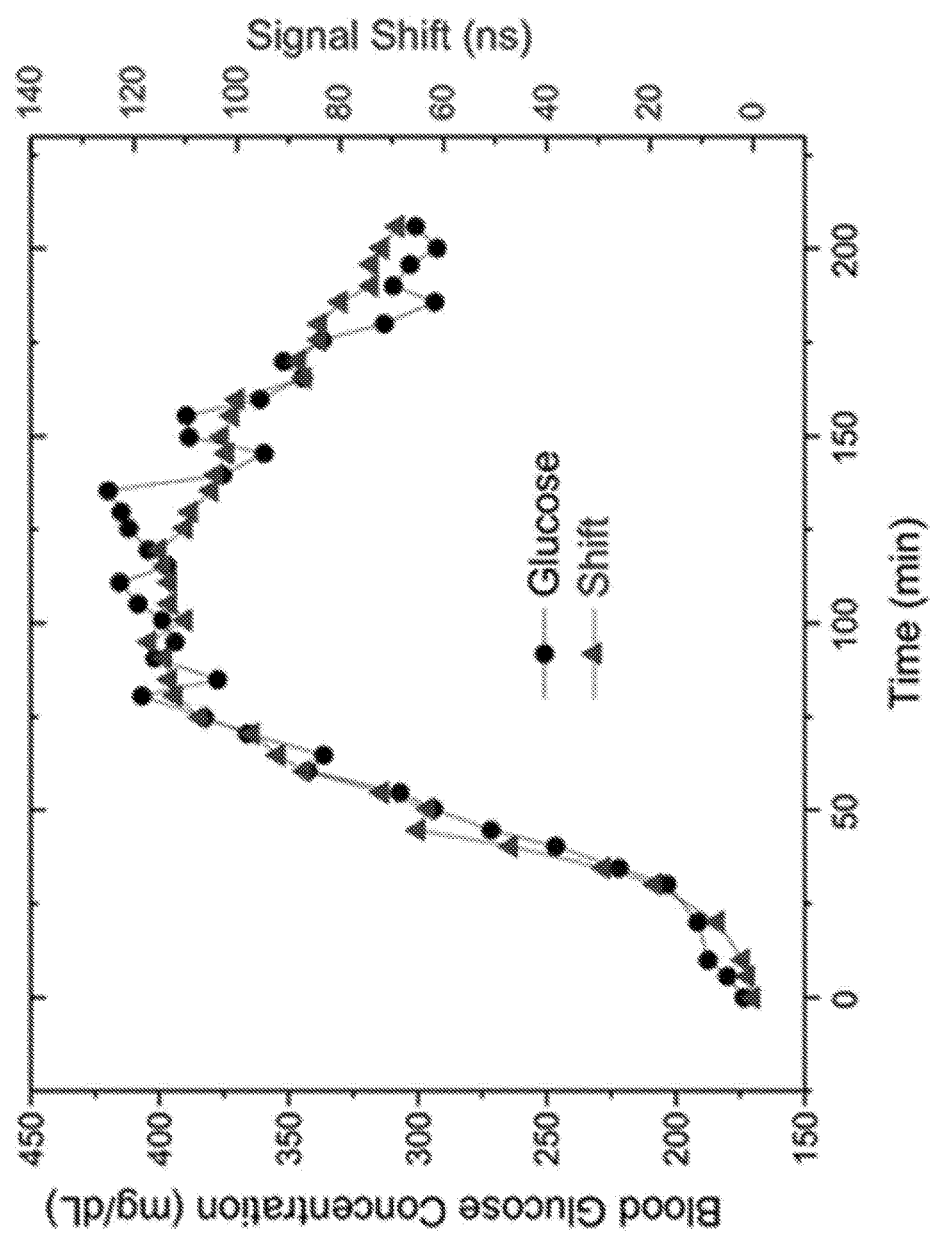
FIG. 3E shows signal shift measured with the ultrasound system GWA and blood glucose concentration obtained from a Type 1 diabetic subject. Blood glucose concentration was measured with two glucose meters (OneTouch Ultra 2 and Ultra Mini) from the same manufacturer (LifeS can, Inc.) and then averaged for the two glucose meters.

FIG. 3E shows average glucose concentration measured invasively with two invasive glucose meters (FreeStyle and OneTouch Ultra 2) and signal shift obtained with the GWA system from a Type 1 diabetic subject. After baseline measurements for first 30 minutes the subject had a breakfast that increased blood glucose concentration from a baseline value of about 140 to 360 mg/dL. The signal shift measured simultaneously with the blood sampling closely followed blood glucose concentration.

Figure 3F:
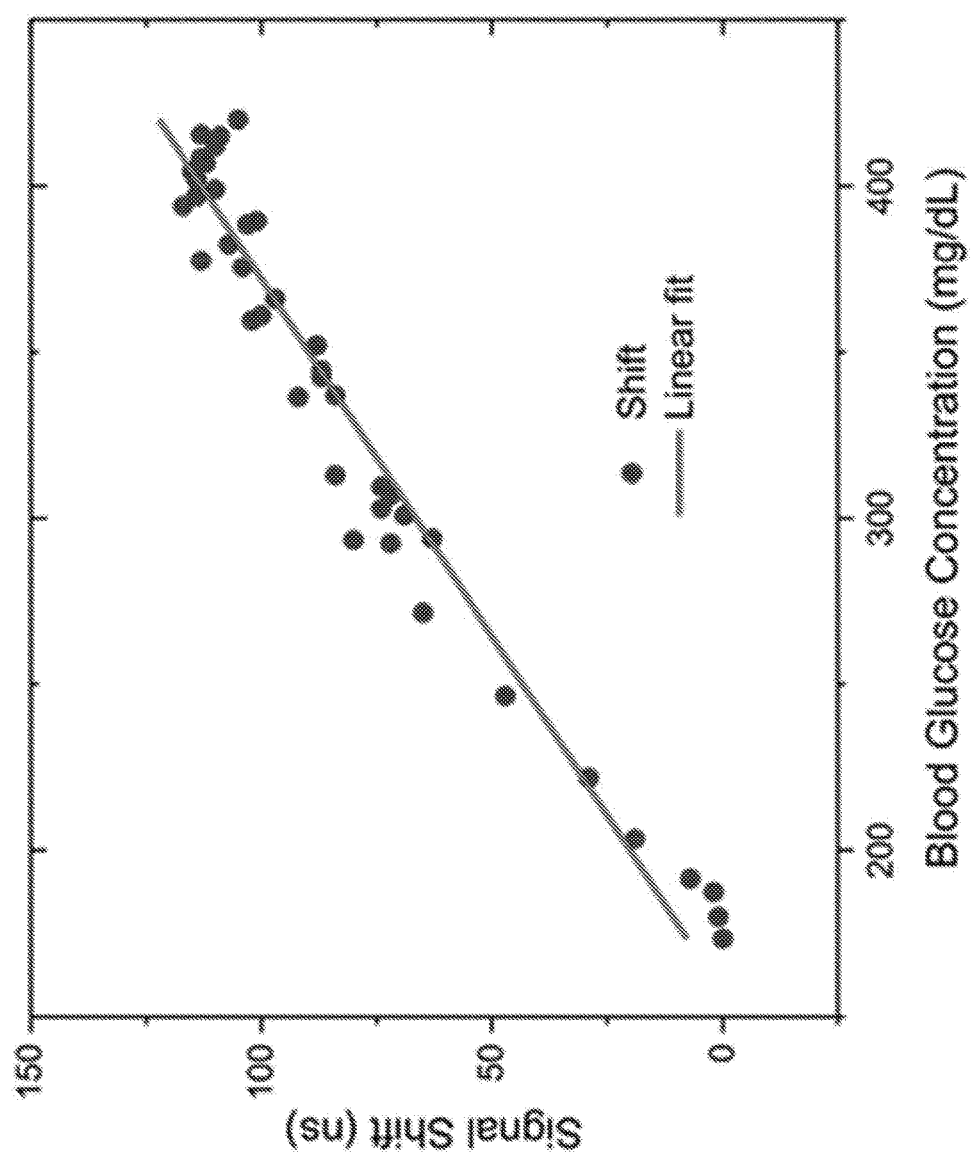
FIG. 3F shows high correlation (R=0.98) of the signal shift with blood glucose concentration obtained from the diabetic subject at minimal motion artefacts, while blood glucose concentration was measured with two glucose meters (OneTouch Ultra 2 and Ultra Mini) from the same manufacturer (LifeScan, Inc.)

FIG. 3F depicts a graph signal shift vs. averaged glucose concentration was plotted based on the data shown in FIG. 3E and linear fit was performed. The data demonstrate linear dependence of the signal shift on the blood glucose concentration and good correlation (R=0.98) between the signal shift and average glucose concentration. Therefore, the signal shift is linearly dependent on blood glucose concentration for diabetic and non-diabetic subjects in the hypo-, normo-, and hyperglycemic concentrations.

Figure 4A:
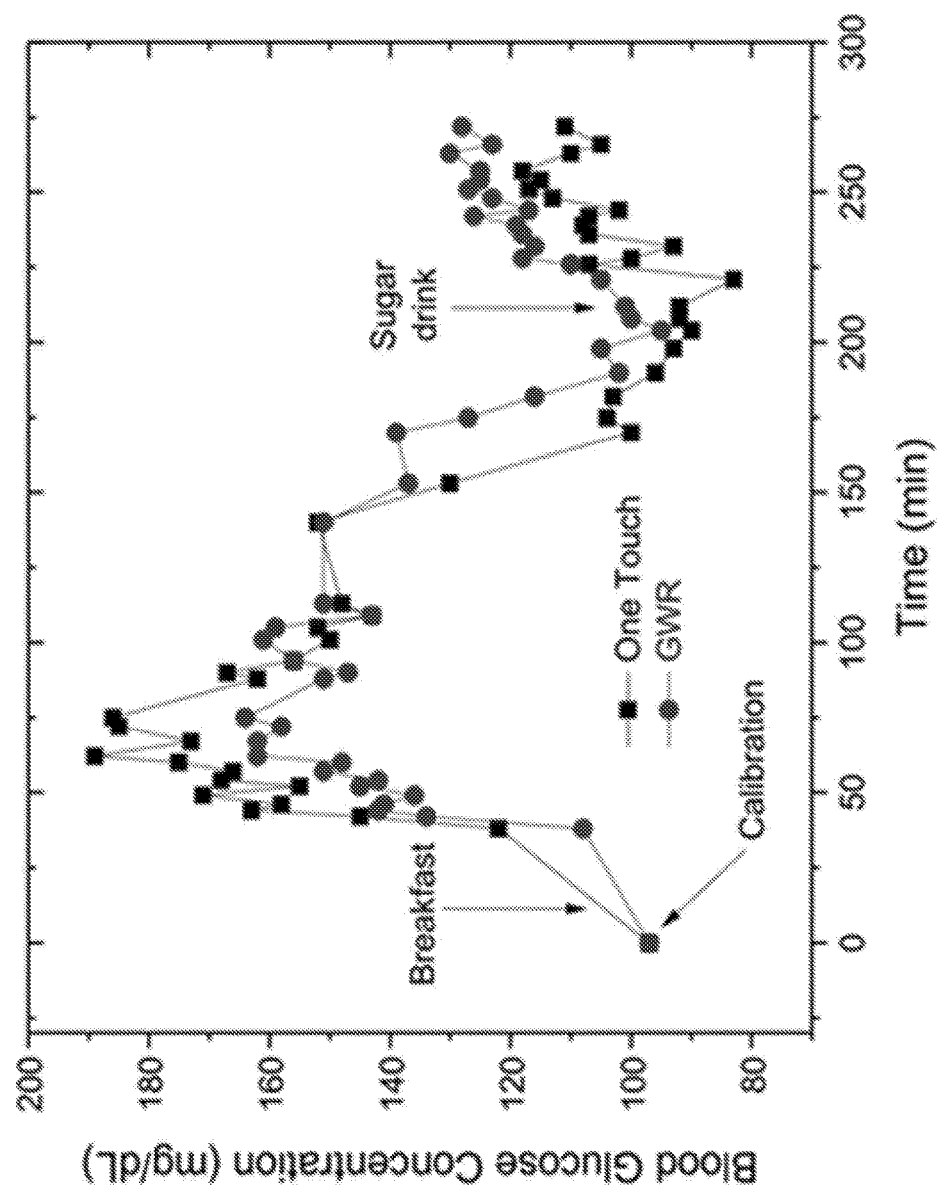
FIG. 4A depicts blood glucose concentration noninvasively measured with a wearable, calibrated ultrasound system GWR after one-point calibration in a non-diabetic subject. Blood glucose concentration was measured with a glucose meter OneTouch Ultra 2.
Figure 4B:
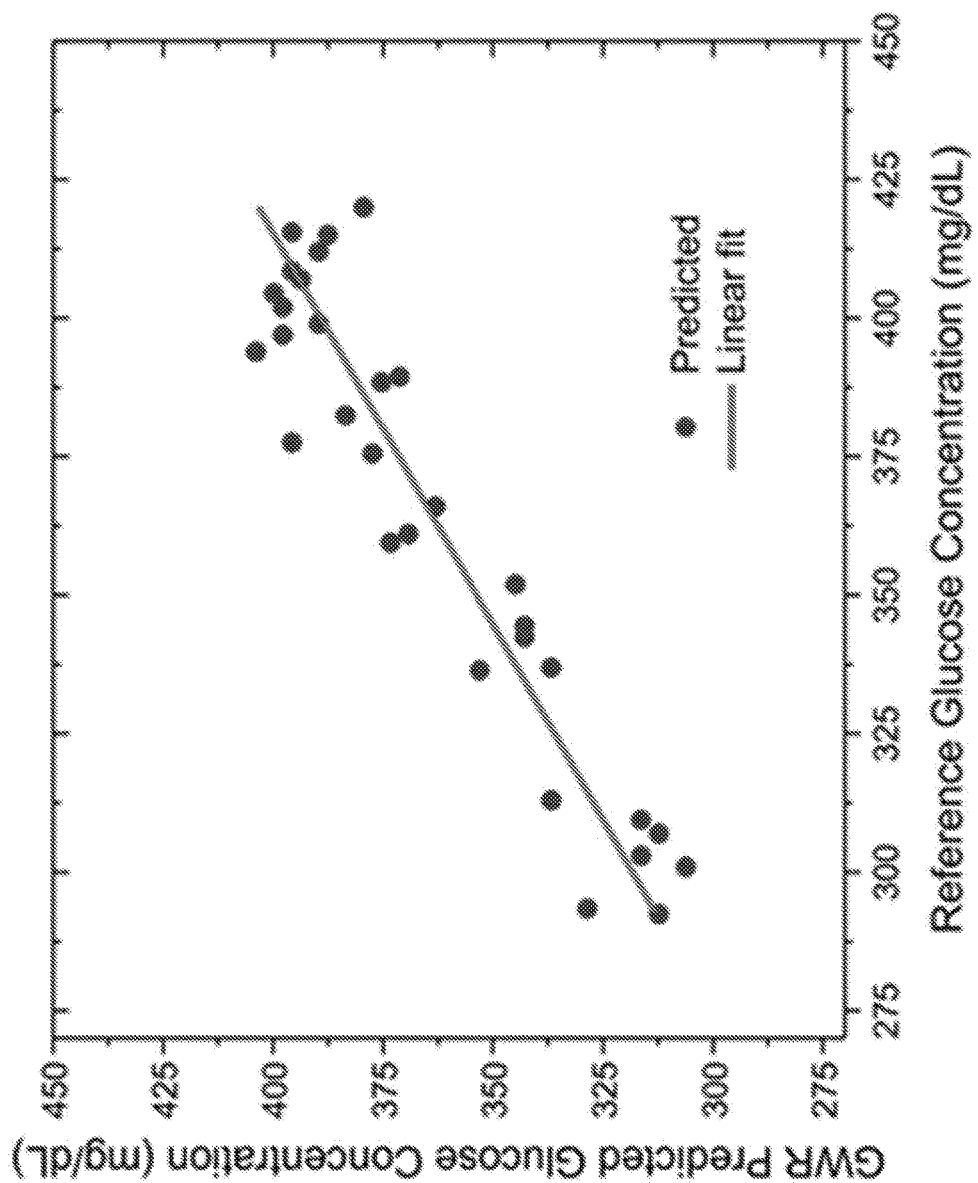
FIG. 4B depicts GWR predicted vs. reference glucose concentration obtained from a Type 2 diabetic subject (R=0.94) using the wearable and calibrated ultrasound system GWR. Clarke Error Grid analysis (data not shown) demonstrated that 100% of the predicted glucose concentrations are within the A zone.
Figure 4C:
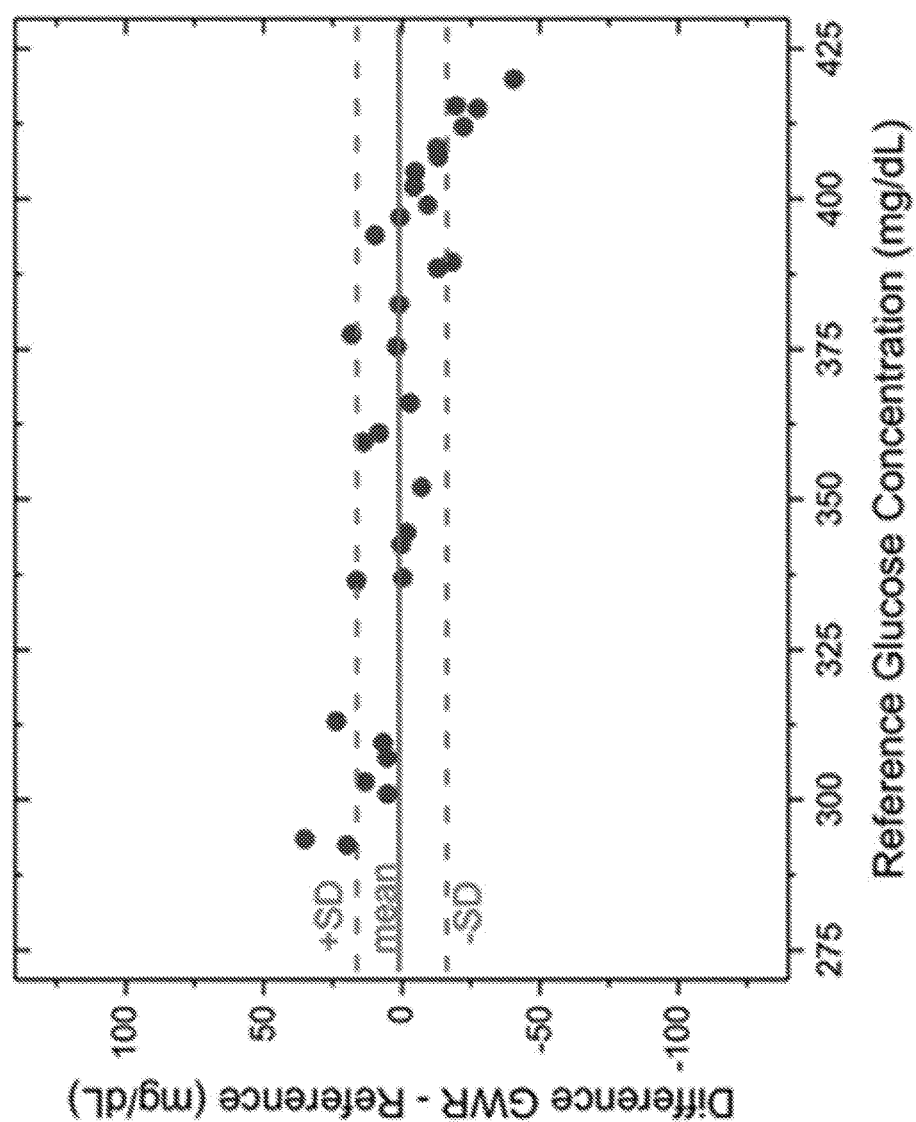
FIG. 4C depicts difference between the GWR predicted and reference glucose concentration vs. reference glucose concentration. The bias (mean) and SD are −0.59 mg/dL and 16 mg/dL, respectively.

Referring now to FIGS. 4A-C, a highly compact (cell phone size), wearable, calibrated version GWR of the ultrasound system shown in FIG. 2B was built and tested in diabetic and non-diabetic subjects.

FIG. 4A depicts glucose concentration noninvasively measured with the ultrasound system GWR after one-point calibration in a non-diabetic subject. Glucose concentration was measured with the glucose meter OneTouch Ultra 2. The subject had a breakfast with high sugar content after the system calibration with one blood sample and then a sugar drink to increase glucose concentration again. The GWR measured glucose concentration had good agreement with the reference values.

FIG. 4B depicts glucose concentration noninvasively measured with the ultrasound system GWR after one-point calibration in a Type 2 diabetic subject. GWR predicted glucose concentration had high correlation (R=0.94) with reference glucose concentration. Clarke Error Grid analysis (data not shown) demonstrates that 100% of the predicted glucose concentrations are within the A zone.

FIG. 4C depicts difference between the GWR predicted and reference glucose concentration vs. reference glucose concentration. The bias (mean) and SD are −0.59 mg/dL and 16 mg/dL, respectively. Therefore, one can conclude that: 1) glucose concentration noninvasively measured with highly compact (cell phone size), wearable, calibrated ultrasound system GWR closely follows reference blood glucose concentration; 2) limited accuracy of the standard glucose meters reduces correlation between the noninvasive and invasive data; and 3) accuracy of noninvasive glucose monitoring with the wearable, calibrated GWR system is approaching that of invasive glucose meters.

Figure 5:
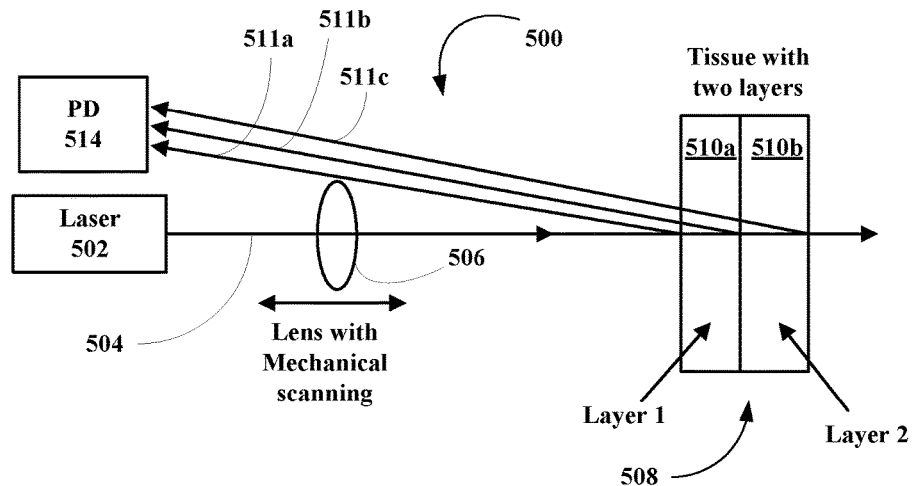
FIG. 5 depicts an embodiment of an optical system for noninvasive glucose monitoring using tissue thickness measurement by a focusing lens with in-depth mechanical scanning Light from a laser or other optical source is focused on the tissue layers. When focus position coincides with tissue boundary, a peak of reflection is induced and is recorded by a photodetector (PD).

Referring now to FIG. 5, another embodiment of a system of this invention, generally 500, is shown to include an is shown to include a pulsed laser light source 502, which produces a pulse beam 504. The pulsed beam 504 passes through a mechanically scanning lens 506 and impinges on a tissue site 508 having layers 510a&b. When focus position coincides with a tissue boundary, a peak of reflection 512a-c is induced and is recorded by a photodetector (PD) 514.

Figure 6:
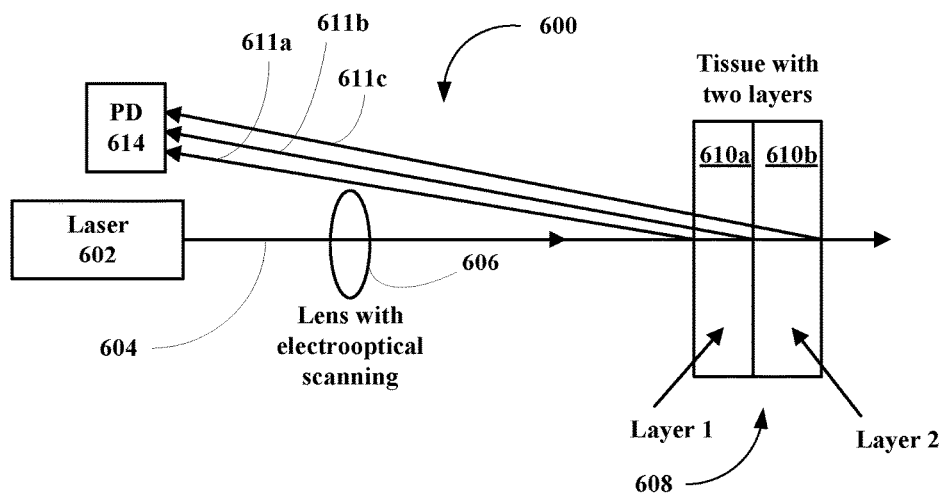
FIG. 6 depicts an optical system for noninvasive glucose monitoring using tissue thickness measurement by a focusing lens with in-depth electrooptical scanning Light from a laser or other optical source is focused on the tissue layers. When focus position coincides with tissue boundary, a peak of reflection is induced and is recorded by a photodetector (PD).

Referring now to FIG. 6, another embodiment of a system of this invention, generally 600, is shown to include a pulsed laser light source 602, which produces a pulse beam 604. The pulsed beam 604 passes through a focusing with in-depth electrooptical scanning lens 606 and impinges on a tissue site 608 having layers 610a&b. When focus position coincides with a tissue boundary, a peak of reflection 612a-c is induced and is recorded by a photodetector (PD) 614.

Figure 7:
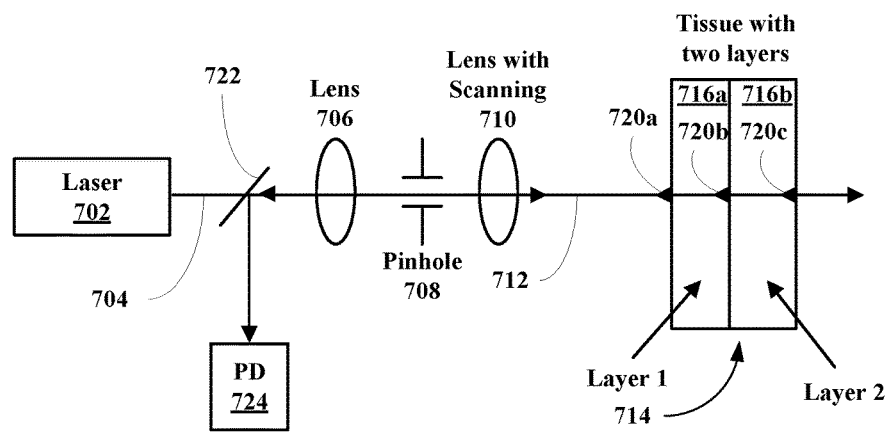
FIG. 7 depicts an optical system for noninvasive glucose monitoring using tissue thickness measurement with a pinhole and a focusing lens with scanning Light from a laser or other optical source is focused through the pinhole on tissue layers. When focus position coincides with tissue boundary, a peak of reflection is induced and is recorded by a photodetector (PD) through the pinhole.

Referring now to FIG. 7, another embodiment of a system of this invention, generally 700, is shown to include a pulsed laser light source 702, which produces a pulse beam 704. The pulsed beam 704 passes through a first lens 706, then through a pinhole 708; and finally, through a focusing with in-depth electrooptical scanning lens 710. The focused beam 712 then impinges on a tissue site 714 having layers 716a&b. When focus position coincides with a tissue boundary, a peak of reflection 720a-c is induced at each boundary. The reflects come back through the scanning lens 710, then the pinhole 708, then the first lens 706 to a dichromic 722 to a photodetector (PD) 724, where is the reflected beam is recorded and analyzed.

Figure 8:
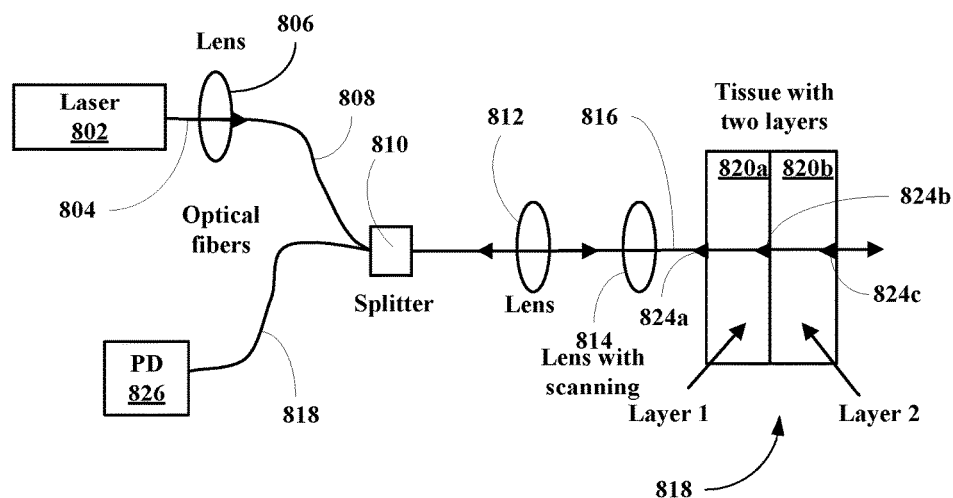
FIG. 8 depicts an optical system for noninvasive glucose monitoring using tissue thickness measurement with a fiber-optic system and a focusing lens with scanning Light from a laser or other optical source is focused through the fiber-optic system on tissue layers. When focus position coincides with tissue boundary, a peak of reflection is induced and is recorded by a photodetector (PD) through the fibers.

Referring now to FIG. 8, another embodiment of a system of this invention, generally 800, is shown to include a pulsed laser light source 802, which produces a pulse beam 804. The pulsed beam 804 passes through a first lens 806, then into a fiber optics fiber 808 and then into a splitter 810. After exiting the splitter 810, the beam 804 proceeds through a second lens 812 and then through a focusing with in-depth electrooptical scanning lens 814. The focused beam 816 then impinges on a tissue site 818 having layers 820a&b. When focus position coincides with a tissue boundary, a peak of reflection 824a-c is induced at each boundary. The reflects come back through the scanning lens 814, then the second lens 812 to the beam splitter 810 to a photodetector (PD) 826, where is the reflected beam is recorded and analyzed.

EXPERIMENTAL SECTION OF THE INVENTION

Example 1

Glucose-induced changes in skin thickness (and/or optical thickness) or time of flight measured with electromagnetic techniques.

Glucose-induced changes in skin tissue thickness (and/or optical thickness) can be measured by using electromagnetic waves including, but not limited to: optical radiation, terahertz radiation, microwaves, radiofrequency waves. Optical techniques include but not limited to reflection, focused reflection, refraction, scattering, polarization, transmission, confocal, interferometric, low-coherence, low-coherence interferometry techniques.

A wearable, like a wrist watch, optically-based glucose sensor can be developed.

Example 2

Glucose-induced changes in time of flight in and thickness of skin measured with ultrasound techniques.

Glucose-induced changes in skin tissue thickness and time of flight can be measured by using ultrasound waves in the frequency range from 20 kHz to 10 Gigahertz. These techniques include but not limited to reflection, focused reflection, refraction, scattering, transmission, confocal techniques. It is well known that by using high frequency ultrasound can provide high-resolution images of tissues. One can use ultrasound frequencies higher than 10 MHz for measurement of skin thickness and time of flight.

FIGS. 1 to 4D show different embodiments of the systems of this invention. In certain embodiments, the typical signal from skin/subcutaneous tissue interface, and glucose-induced signal shift (changes in time of flight) measured by the system. In other embodiments, compact ultrasound generators and sensors may be associated with wearable devices such as wrist watch, contact lens, or sensor attached to other parts of the body for implementing ultrasound-based glucose sensor with wearable devices.

Example 3

Glucose-induced changes in skin thickness and time of flight measured with optoacoustic or thermoacoustic techniques.

Figure 10:
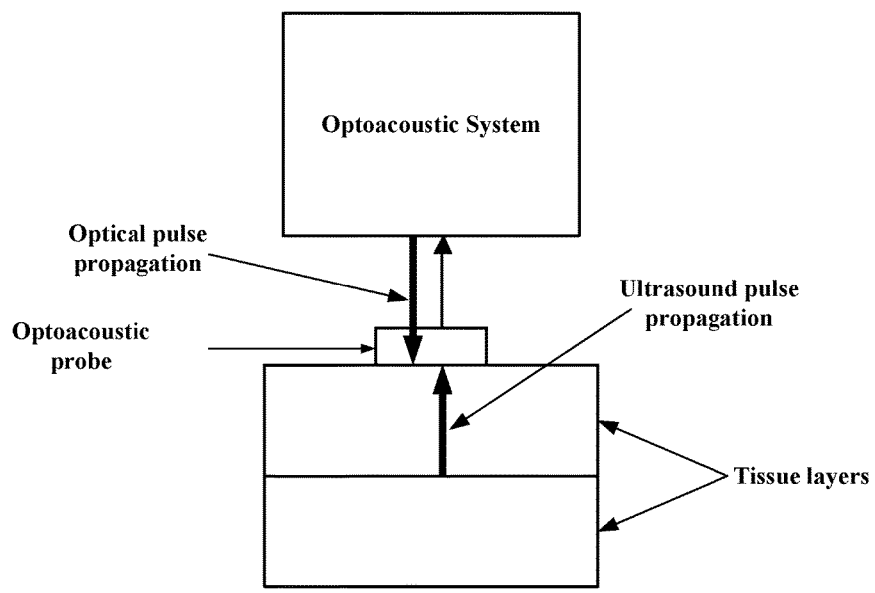
FIG. 10 depicts an optoacoustic system for time of flight or thickness measurements. At least one short (typically nanosecond or picosecond) optical pulse is generated by the system, directed to the tissue, generates ultrasound waves in the tissues. An ultrasound transducer detects the ultrasound waves and the ultrasound signal is analyzed by a processor. The optically-induced ultrasound waves carry information on the ultrasound time of flight in tissue layers. The geometrical thickness can be calculated by multiplying the time of flight by speed of sound.

Glucose-induced changes in skin tissue thickness and time of flight can be measured by using optoacoustic or thermoacoustic techniques which may provide accurate tissue dimension measurement when short electromagnetic (optical or microwave) pulses are used in combination with wide-band ultrasound detection. FIG. 10 shows such a system. Optical detection of the ultrasound waves can be used instead of the ultrasound transducer.

Example 4

Glucose-induced changes in the lens and anterior chamber thickness (and/or optical thickness) measured with optical techniques.

One can use measurement of eye tissue thickness and/or optical thickness with optical techniques for noninvasive and accurate glucose monitoring. The preferred embodiment is glucose monitoring by measuring thickness of the lens and/or anterior chamber or their ratio by using non-contact reflection techniques, preferably with focused light reflection technique. The focused reflection technique utilizes focused light for tissue irradiation and detection of reflection peaks (maxima) when the light is focused on tissue surfaces. If the focus is scanned in depth, one can measure tissue thickness by recording and analyzing the peaks of reflections during the scanning. This technique allows for measurement of tissue thickness with high (submicron) accuracy. One can use multiple detectors to increase signal-to-noise ratio and, therefore, accuracy of glucose monitoring. This technique can be used for tissue thickness measurement (as well as optical thickness measurements) in other tissues (not only eye tissues).

The focused light reflection technique in its simplest form can utilize a light beam focused with a lens on a tissue surface and detection of the reflected light with at least one optical detector positioned at a small angle with respect to the incident beam. By in-depth scanning the focus, one can detect peaks of reflected light intensity when the focus reaches a tissue surface, or a tissue layer surface. FIG. 5 shows such a system which utilizes a lens with mechanical scanning One can use a lens with electrooptical scanning that provides fast in-depth scanning and with no moving parts (FIG. 6). A voltage is applied to the lens to vary the focus position within the tissue by using electrooptical effects.

Another modification of this technique is to use a pinhole that may provide higher signal-to-noise ratio by reducing stray light and background tissue scattering light (FIG. 7). Instead of a pinhole one can use a fiber-optic system (FIG. 8) that may provide high signal-to-noise ratio too. Similar fiber-optic system was used by Zeibarth et al. It was demonstrated that such a system can measure eye tissue thickness (including the lens) with high (submicron) accuracy (Zeibarth et al.).

Furushima et al. demonstrated using ultrasound techniques (with submillimeter resolution) that the thickness of the lens increases, while thickness of anterior chamber decreases with blood glucose concentration. Therefore, one can monitor noninvasively glucose concentration with high accuracy and sensitivity by using the measurement of lens and anterior chamber thickness with either the focused light reflection technique or the focus-detection technique. The system (either the focused light reflection system or the focus-detection system) can be assembled on glasses or other wearable device to provide convenient and continuous measurement.

Example 5

Glucose-induced changes in the lens and anterior chamber thickness measured with ultrasound techniques.

High frequency ultrasound (>10 MHz) can be used for glucose monitoring based on measurement of the lens and/or anterior chamber thickness or time of flight in these tissues. Focused reflection technique utilizing focused ultrasound can be applied too to provide higher resolution.

Example 6

Glucose-induced changes in the skin or lens and anterior chamber thickness or time of flight measured with optoacoustic or thermoacoustic techniques (FIG. 10).

The optoacoustic and thermoacoustic techniques can provide acceptable accuracy of the thickness or time of flight measurement in these tissues if short optical (or microwave, or radiofrequency) pulse are used for generation of the thermoelastic waves and if detection of these waves is performed with wide-band, high-frequency ultrasound detectors. Focused radiation can be used to provide better accuracy of measurement.

Optical detection of the optoacoustic or the thermoelastic waves can be used to provide non-contact measurement of the optoacoustic and the thermoelastic waves. The non-contact optical detection is more preferable for detecting these waves induced in the eye tissues compared to detection by ultrasound transducers because it minimizes discomfort for the patient.

Example 7

Figure 9:
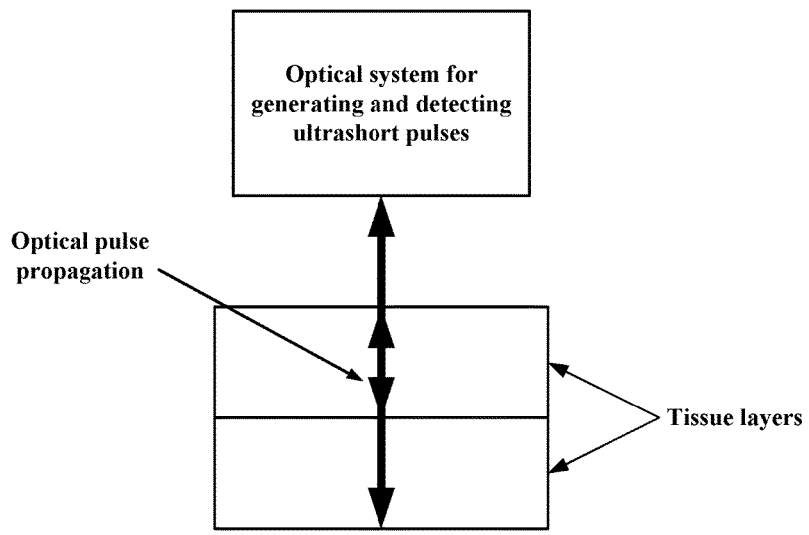
FIG. 9 depicts a time-resolved optical system generating ultrashort (typically femtosecond) optical pulses, directing the pulses to the tissues, and detecting the pulses reflected from tissue layers. The system measures the time of flight of the optical pulses and converts them into blood glucose concentration.

A time-resolved optical system (FIG. 9) can be used for glucose monitoring in the tissues, preferably the tissues of the eye. The system generates ultrashort (typically femtosecond) optical pulses, directs the pulses to the tissues, and detects the pulses reflected from tissue layers. The system measures the time of flight of the optical pulses and converts them into blood glucose concentration.

Example 8

An optical system for generating short, broad-band ultrasound pulses in an optically absorbing medium (FIG. 11) can be used for glucose monitoring. The medium is attached to the skin surface. The optical system produces at least one short (typically nanosecond or picosecond) optical pulse and directs it on the absorbing medium. The energy of the optical pulse is absorbed by the medium that results in generation of a short ultrasound (acoustic) pulse. The ultrasound pulse then propagates in the tissue and is reflected from tissue layers. An ultrasound transducer detects the reflected ultrasound pulses and a processor analyzes the signal from the transducer and calculates the time of flight of the ultrasound pulses and glucose concentration.

A short (typically nanosecond) radiofrequency electromagnetic pulse can be used instead of the short optical pulse to generate a short, broad-band ultrasound pulse in a radiofrequency absorbing medium.

An optical detection of the reflected ultrasound pulses can be used.

The existing techniques for glucose monitoring are invasive. For last 30 years many noninvasive glucose monitoring techniques have been proposed, however they suffer from insufficient accuracy, sensitivity, and specificity. At present, there is no noninvasive glucose monitor on the market.

The methods of the present invention can be practiced so that the measurements include attenuation, phase, and frequency of the reflected and incident beams or beam pulses.

Wearable Glucose Monitors

Embodiments of this invention relate to systems for noninvasive glucose sensing comprising a wearable glucose monitor including an ultrasound source and a ultrasound detector and a feedback unit. In certain embodiments, the ultrasound source generating ultrasound in the frequency range from about 20 kHz to about 10 Gigahertz with one, two, or multiple frequencies or broad-band ultrasound generated by a piezoelectric element, or by short electromagnetic pulses irradiating a strongly absorbing medium. In other embodiments, the systems further comprising an electromagnetic source generating electromagnetic pulses or waves are optical radiation (near infrared, infrared, far infrared, visible, or UV light in the wavelength range from about 200 nanometers to about 100 microns), terahertz waves, microwaves, radiowaves, low-frequency waves, static electric or magnetic field or combination of different waves with one, two, or multiple wavelengths (frequencies). In other embodiments, the measurement of time of flight of said ultrasound or optical pulses or measurement of tissue dimension is combined with measurement of attenuation, phase, and frequency spectrum of the ultrasound or optical pulses reflected from or transmitted through the tissues to improve accuracy and specificity of glucose monitoring. In other embodiments, the target tissue includes but not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue. In other embodiments, the ultrasound or electromagnetic pulses or waves are detected using reflection, focused reflection, refraction, scattering, polarization, transmission, confocal, interferometric, low-coherence, low-coherence interferometry techniques. In other embodiments, the electromagnetic pulses are ultrashort in the range from about 1 femtosecond to about 1 microsecond to provide accurate time of flight or dimension measurement.

Embodiments of this invention related to methods for noninvasive glucose sensing including the steps of providing a noninvasive glucose sensing system comprising a wearable glucose monitor including an ultrasound source and a ultrasound detector and a feedback unit; measuring time of flight of ultrasound or electromagnetic pulses (or waves) in a target tissue or measuring at least one dimension of a target tissue using ultrasound or electromagnetic pulses (or waves); and determining a glucose value from the time of flight in the target tissue in accordance with a time of flight versus glucose calibration curve or determining a glucose value from the dimension of the target tissue in accordance with the dimension versus glucose calibration curve. In certain embodiments, the ultrasound is in the frequency range from about 20 kHz to about 10 Gigahertz with one, two, or multiple frequencies or broad-band ultrasound generated by a piezoelectric element, or by short electromagnetic pulses irradiating a strongly absorbing medium. In other embodiments, the electromagnetic pulses or waves are optical radiation (near infrared, infrared, far infrared, visible, or UV light in the wavelength range from about 200 nanometers to about 100 microns), terahertz waves, microwaves, radiowaves, low-frequency waves, static electric or magnetic field or combination of different waves with one, two, or multiple wavelengths (frequencies). In other embodiments, the measurement of time of flight of said ultrasound or optical pulses or measurement of tissue dimension is combined with measurement of attenuation, phase, and frequency spectrum of the ultrasound or optical pulses reflected from or transmitted through the tissues to improve accuracy and specificity of glucose monitoring. In other embodiments, the target tissue includes but not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, and/or tendon tissue. In other embodiments, the ultrasound or electromagnetic pulses or waves are detected using reflection, focused reflection, refraction, scattering, polarization, transmission, confocal, interferometric, low-coherence, and/or low-coherence interferometry techniques. In other embodiments, the electromagnetic pulses are ultrashort in the range from about 1 femtosecond to about 1 microsecond to provide accurate time of flight or dimension measurement.

Embodiments of this invention relate to wearable noninvasive glucose monitoring systems based on the measurement of dimensions or time of flight in tissue using ultrasound, optical, or optoacoustic technique where dimensions of time of flight are measured in at least one tissue or tissue layer in skin (dermis, epidermis, subcutaneous connective tissue, subcutaneous fat, subcutaneous muscle), eye (lens, anterior chamber, vitreous cavity, eye ball, sclera), mucosal tissues, nailbed, lunula, connective tissue, muscle tissue, blood vessels, cartilage tissue, and/or tendon tissue. In certain embodiments, the wearable, noninvasive glucose monitoring method is applied to a wrist area. In other embodiments, the systems comprise a wrist watch or incorporated in a wrist watch and provides current glucose concentration and/or a graph of glucose concentration vs. time by probing skin and/or subcutaneous tissues such as dermis, epidermis, subcutaneous connective tissue, subcutaneous fat tissue, subcutaneous muscle tissue. In other embodiments, the wearable, noninvasive glucose monitoring system can wirelessly communicate with a cell phone which can show the current glucose concentration and/or a graph of glucose concentration vs. time. In other embodiments, the wearable, noninvasive glucose monitoring method is applied to at least one eye tissue or tissue layer. In other embodiments, wearable monitoring system comprises a contact lens and the system is incorporated in a contact lens that can provide glucose monitoring by probing the cornea, eye lens, iris, sclera, retina, and/or eye ball and displays a current glucose concentration and/or a graph of glucose concentration vs. time. In other embodiments, the systems wirelessly communicate with a cell phone or a wrist watch that can show the current glucose concentration and/or a graph of glucose concentration vs. time. In other embodiments, the wearable, noninvasive glucose monitoring method is applied to at least one tissue or tissue layer in an arm, forearm, wrist, shoulder, hand, palm, finger, abdomen, chest, neck, head, ear, back, leg, and/or foot. In other embodiments, the systems communicate wirelessly to medical personnel in a health care facility or not in a health care facility and the medical personnel can contact the patient and/or provide medical care, if necessary. In other embodiments, the wearable noninvasive glucose monitoring system is incorporated with at least one monitor of at least one parameter such as pulse rate, blood oxygenation, body temperature, and/or blood pressure, and the monitors can wirelessly communicate with a cell phone which can show the current value of at least one parameter and a graph of at least one parameter vs. time. In other embodiments, the monitors can provide information to said noninvasive glucose monitoring system for more accurate glucose concentration monitoring. In other embodiments, the noninvasive glucose monitoring system and/or at least one said monitor can wirelessly communicate with a cell phone and/or with medical personnel in a health care facility or not in a health care facility; and the medical personnel can contact the patient and/or provide medical care, if necessary. The wearable, noninvasive glucose monitoring system is incorporated in an insulin patch or insulin pump. The glucose monitor provides the glucose concentration values to the insulin patch or insulin pump to adjust the rate of insulin administration to control blood glucose concentration. In other embodiments, the insulin patch or insulin pump is attached to the inner wrist area where the blood vessels are large and close to skin surface to provide rapid and more controllable insulin administration in blood. In other embodiments, the monitor and the insulin patch or the insulin pump work in a closed-loop mode for more accurate glucose control. In other embodiments, the glucose monitoring systems may incorporate an invasive meter for calibration of the glucose monitor using a blood or interstitial fluid sample. In other embodiments, the invasive meter provides values of glucose, urea, ions of sodium, potassium, chloride for more accurate monitoring of glucose concentration with the noninvasive glucose monitoring system. In other embodiments, the wearable, noninvasive glucose monitoring system is attached to the abdomen area and provides the glucose concentration values to the insulin patch or insulin pump to adjust the rate of insulin administration to control blood glucose concentration. In other embodiments, the monitor and the insulin patch or insulin pump communicate with the cell phone which can show the current glucose concentration, and/or a graph of glucose concentration vs. time, and/or and at least one insulin administration parameter such as insulin administration rate. In other embodiments, the monitor and the insulin patch or the insulin pump work in a closed-loop mode for more accurate glucose control. In other embodiments, the system incorporates an invasive meter for calibration of the glucose monitor and the invasive meter uses at least one blood and or interstitial fluid sample to provide values of concentration of glucose, urea, ions of sodium, potassium, chloride for more accurate monitoring of glucose concentration.

Detailed Description of Wearable Monitor Figures

FIG. 12A depicts a wearable, noninvasive glucose monitoring system including a glucose sensor of this invention shown here as a wrist watch or incorporated in a wrist watch, where the glucose sensor is located on the back of the watch (not shown). The system may display a current glucose concentration by probing skin and/or subcutaneous tissues including, without limitation, dermis, epidermis, subcutaneous connective tissue, subcutaneous fat tissue, and combinations thereof.

FIG. 12B depicts a wearable, noninvasive glucose monitoring system shown here as a wrist watch or incorporated in a wrist watch that may wirelessly communicate with a cell phone, which may display a current glucose concentration and a graph of glucose concentration vs. time.

FIG. 13 shows a wearable, noninvasive glucose monitoring system incorporated in a contact lens that including a glucose sensor for monitoring glucose concentrations by probing eye tissue including, without limitation, cornea, eye lens, iris, sclera, and/or retina. The system may also wirelessly communicate with a cell phone which may, which may display a current glucose concentration and a graph of glucose concentration vs. time.

FIG. 14 depicts a wearable, noninvasive glucose monitoring system incorporated in a pair of glasses that may provide glucose monitoring by probing eye tissue including, without limitation, cornea, eye lens, iris, sclera, and/or retina. The system shows to the patient a current glucose concentration and a graph of glucose concentration vs. time in a heads up display in the glasses. The system may also wirelessly communicate with a cell phone, which may display the current glucose concentration and a graph of glucose concentration vs. time.

FIG. 15 depicts a wearable, noninvasive glucose monitoring system shown here as a wrist watch or incorporated in the wrist watch that may wirelessly communicate with a cell phone, which may display a current glucose concentration and a graph of glucose concentration vs. time. A noninvasive glucose sensor may be attached or affixed to an arm, forearm, or any other site of the body. The system or the cell phone may also communicate wirelessly to medical personnel in a health care facility or not in a health care facility. The medical personnel may contact the patient and/or provide medical care, if necessary.

FIG. 16 depicts a wearable, noninvasive glucose monitoring system associated with a wrist watch or incorporated in a wrist watch with other monitors including, without limitation, vital signs monitors of pulse rate, blood oxygenation, body temperature, and/or blood pressure. The monitors may wirelessly communicate with a cell phone, which may display a current glucose concentration and a graph of glucose concentration vs. time. Moreover, the monitors may provide information to the noninvasive glucose monitoring system for more accurate glucose concentration monitoring. The systems or the cell phone may also communicate wirelessly to medical personnel in a health care facility or not in a health care facility. The medical personnel can contact the patient and/or provide medical care, if necessary.

FIG. 17 depicts a wearable, noninvasive glucose monitoring system associated with a wrist watch or incorporated in a wrist watch with insulin patch or insulin pump. The monitor provides the glucose concentration values to the insulin patch or insulin pump to adjust the rate of insulin administration to control blood glucose concentration. In certain embodiments, the insulin patch or insulin pump is attached to the inner wrist area where the blood vessels are large and close to skin surface that will provide rapid and more controllable insulin administration in blood. The monitor and the insulin patch or the insulin pump may work in a closed-loop mode for more accurate glucose control. Moreover, the system may incorporate an invasive meter for calibration of the glucose monitor. The invasive meter uses a blood sample(s) to provide values of blood analytes including but not limited to blood or interstitial fluid concentration of glucose, urea, ions of sodium, potassium, chloride for more accurate monitoring of glucose concentration with the noninvasive glucose monitoring system.

FIG. 18 depicts a wearable, noninvasive glucose monitoring system attached to a stomach area. The monitor provides the glucose concentration values to the insulin patch or insulin pump to adjust the rate of insulin administration to control blood glucose concentration. The monitor and the insulin patch of pump can communicate with the cell phone which can show the current glucose concentration, a graph of glucose concentration vs. time, and insulin administration parameters including but limited to insulin administration rate. The monitor and the insulin patch or the insulin pump may work in a closed-loop mode for more accurate glucose control. Moreover, the system may incorporate an invasive meter for calibration of the glucose monitor. The invasive meter uses a blood sample(s) to provide values of blood analytes including but not limited to blood or interstitial fluid concentration of glucose, urea, ions of sodium, potassium, chloride for more accurate monitoring of glucose concentration with the noninvasive glucose monitoring system.

REFERENCES CITED IN THE INVENTION

Ziebarth N., Manns F., Parel J.-M. Fibre-optic focus detection system for non-contact, high resolution thickness measurement of transparent tissues. Journal of Physics D: Applied Physics, 2005, v. 38, pp 2708-2715.

Furushuma M., Imazumi M., Nakatsuka K Changes in Refraction Caused by Induction of Acute Hyperglycemia in Healthy Volunteers. Japanese Journal of Ophthalmology, 1999, v 43, pp 398-403.

Van den Berghe G, Schoonheydt K, Becx P, Bruyninckx F, Wouters P J. Insulin therapy protects the central and peripheral nervous system of intensive care patients. *Neurology.* 2005 Apr. 26; 64(8):1348-53.

Vanhorebeek I, Langouche L, Van den Berghe G. Glycemic and nonglycemic effects of insulin: how do they contribute to a better outcome of critical illness? *Curr Opin Crit Care.* 2005 August; 11(4):304-11.

van den Berghe G, Wouters P, Weekers F, Verwaest C, Bruyninckx F, Schetz M, Vlasselaers D, Ferdinande P, Lauwers P, Bouillon R. Intensive insulin therapy in the critically ill patients. *N Engl J Med.* 2001 Nov. 8; 345 (19):1359-67.

CLOSING PARAGRAPH

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. A wearable apparatus for glucose sensing comprising:
   (a) a noninvasive glucose sensor, adapted to be in contact with or attached to a target tissue, comprising:
      (i) an ultrasound generator configured to direct ultrasound pulses or waves into the target tissue, and
      (ii) an ultrasound detector configured to:
         (1) detect ultrasound pulses or waves reflected from the target tissue using reflection, focused reflection, refraction, scattering, polarization, transmission, confocal, interferometric, low-coherence, and/or a low-coherence interferometry technique, and
         (2) generate a signal corresponding to the detected ultrasound pulses or waves,
   (b) a processor configured to:
      (i) receive the signal from the ultrasound detector,
      (ii) measure:
         (1) at least one time of flight of the ultrasound pulses or waves reflected from or transmitted through the target tissue evidencing boundaries or interfaces within the target tissue, and/or
         (2) at least one dimension of the target tissue evidencing a specific tissue layer within the target tissue, wherein the dimension includes thickness, length, width, diameter, curvature, or roughness; and
      (iii) determine a glucose concentration value from:
         (1) the at least one measured time of flight, and/or
         (2) the at least one measured dimension, and
   (c) a feedback unit including a display and configured to display a current glucose value or a plot of glucose values versus time,
   wherein the target tissue is associated with an arm, a forearm, a wrist, a shoulder, a hand, a palm, a finger, an abdomen, a chest, a neck, a head, an ear, an eye, a back, a leg, a foot, or mixtures and combinations thereof, and
   wherein target tissue comprises a skin tissue, an eye tissue, a mucosal tissue, a nail bed, a lunula, a connective tissue, a muscle tissue, a blood vessel, a cartilage tissue, a tendon tissue, or mixtures and combinations thereof.

2. The apparatus of claim 1, wherein the ultrasound pulses or waves have a frequency range from about 20 kHz to about 10 Gigahertz, the ultrasound pulses or waves comprise two or multiple frequencies within the frequency range or a broad-band of frequencies within the frequency range.

3. The apparatus of claim 1, wherein the ultrasound generator comprises: (1) a piezoelectric element adapted to direct ultrasound pulses or waves into the target tissue, (2) a light source adapted to direct optical pulses into the target tissue to generate thermoelastic ultrasound pulses or waves within the target tissue, (3) a light source adapted to direct optical pulses into an optically absorbing medium to generate ultrasound pulses or waves directed into the target tissue, or (4) a radiofrequency source adapted to direct radiofrequency pulses into a radiofrequency absorbing medium to generate ultrasound pulses or waves directed into the target tissue and wherein all of the pulses are in the range from about 1 femtosecond to about 1 microsecond.

4. The apparatus of claim 1, wherein:
   the glucose sensor, the processor, and the feedback unit are integral to form an integral apparatus, or
   the glucose sensor is separate from the processor and feedback unit to form a separated apparatus, wherein the sensor is configured to transmit the signal to the processor.

5. The apparatus of claim 4, wherein:
   the integral apparatus comprises:
      a wrist watch further comprising an invasive glucose sensor configured to use blood or interstitial fluid to calibrate the noninvasive glucose sensor, or
      a pair of glasses, wherein the feedback unit is a head up display associated with the glasses, or
   the separated apparatus comprises a contact lens including the noninvasive glucose sensor.

6. The apparatus of claim 5, wherein the wrist watch further comprises of a pulse rate monitor, a blood oxygenation monitor, a body temperature monitor, and/or a blood pressure monitor.

7. The apparatus of claim 6, wherein the monitors of pulse rate, blood oxygenation, body temperature, and/or blood pressure wirelessly communicate with a cell phone which displays current glucose concentration and a graph of glucose concentration vs. time.

8. The apparatus of claim 7, wherein the monitors or cell phone communicate wirelessly with a health care facility or a non-health care facility.

9. The apparatus of claim 1, further comprising:
(d) an insulin patch or an insulin pump under control of the processor.

10. The apparatus of claim 1, wherein the processor is further configured to transmit the current glucose concentration and/or the graph to medical personnel.

11. The apparatus of claim 1, wherein the glucose concentration value is determined from:
(a) the at least one ultrasound time of flight in accordance with an ultrasound time of flight versus glucose calibration curve, and
(b) the at least one ultrasound dimension in accordance with an ultrasound dimension versus glucose calibration curve.

12. A method for noninvasive glucose sensing comprising the steps of:
generating ultrasound pulses or waves using a wearable apparatus comprising:
(a) a noninvasive glucose sensor, adapted to be in contact with or attached to a target tissue, comprising:
(i) an ultrasound generator configured to direct ultrasound pulses or waves into the target tissue, and
(ii) an ultrasound detector configured to:
(1) detect ultrasound pulses or waves reflected from the target tissue using reflection, focused reflection, refraction, scattering, polarization, transmission, confocal, interferometric, low-coherence, and/or a low-coherence interferometry technique, and
(2) generate a signal corresponding to the detected ultrasound pulses or waves,
(b) a processor configured to:
(i) receive the signal from the ultrasound detector and measure:
(1) at least one time of flight of the ultrasound pulses or waves reflected from or transmitted through the target tissue evidencing boundaries or interfaces within the target tissue, and/or
(2) at least one dimension of the target tissue evidencing a specific tissue layer within the target tissue, wherein the dimension includes thickness, length, width, diameter, curvature, or roughness, and
(ii) determine a glucose concentration value from:
(1) the at least one measured time of flight, and/or
(2) the at least one measured dimension, and
(c) a feedback unit including a display and configured to display a current glucose value or a plot of glucose values versus time,
directing the ultrasound pulses or waves into the target tissue;
detecting:
(a) reflected, refracted, scattered, back-scattered, or forward-scattered ultrasound pulses or waves from the target tissue using the ultrasound detector, and/or
(b) transmitted ultrasound pulses or waves passing through target tissue using the ultrasound detector;
measuring:
(a) at least one ultrasound time of flight based on the detected ultrasound pulses or waves evidencing boundaries or interfaces within the target tissue or passing through the target tissue based on changes in the ultrasound pulses or waves at the boundaries or interfaces using a processor, and/or
(b) at least one ultrasound dimension of a specific tissue layer within the target tissue including a thickness, length, width, diameter, curvature, or roughness based on the detected ultrasound pulses or waves using the processor; and
determining a glucose concentration value from:
(a) the at least one ultrasound time of flight in, and/or
(b) the at least one ultrasound dimension,
wherein the target tissue is associated with an arm, a forearm, a wrist, a shoulder, a hand, a palm, a finger, an abdomen, a chest, a neck, a head, an ear, an eye, a back, a leg, a foot, or mixtures and combinations thereof.

13. The method of claim 12, wherein:
the measuring step comprises measuring:
(a) the at least one ultrasound time of flight based on the detected ultrasound pulses or waves evidencing the boundaries or interfaces within the target tissue using the processor, and
(b) the at least one ultrasound dimension of the specific tissue layer within the target tissue based on the detected ultrasound pulses or waves using the processor, where the ultrasound dimension includes thickness, length, width, diameter, curvature, or roughness, and
the determining step comprises determining a glucose concentration value from:
(a) the at least one ultrasound time of flight in accordance with an ultrasound time of flight versus glucose calibration curve, and
(b) the at least one ultrasound dimension in accordance with an ultrasound dimension versus glucose calibration curve.

14. The method of claim 12, further comprising:
measuring an attenuation, a phase, and a frequency spectrum of the detected ultrasound pulses or waves to improve an accuracy and specificity of the glucose concentration value.

15. The method of claim 12, wherein, in the generating, directing, detecting, measuring, and determining steps, the target tissue comprises a skin tissue, an eye tissue, a mucosal tissue, a nail bed, a lunula, a connective tissue, a muscle tissue, a blood vessel, a cartilage tissue, or a tendon tissue and wherein the skin tissue includes a dermis, an epidermis, or subcutaneous fat and the eye tissue includes a lens, an anterior chamber, a vitreous cavity, an eye ball, or a sclera.

16. The method of claim 12, wherein, in the generating, directing, detecting, measuring, and determining steps, the ultrasound pulses or waves have a frequency range from about 20 kHz to about 10 Gigahertz, the ultrasound pulses or waves comprise two or multiple frequencies within the frequency range or a broad-band of frequencies within the frequency range.

17. The method of claim 12, wherein, in the generating step, the ultrasound generator comprises: (1) a piezoelectric element adapted to direct ultrasound pulses or waves into the target tissue, (2) a light source adapted to direct optical pulses into the target tissue to generate thermoelastic ultrasound pulses or waves within the target tissue, (3) a light source adapted to direct optical pulses into an optically absorbing medium to generate ultrasound pulses or waves directed into the target tissue, or (4) a radiofrequency source adapted to direct radiofrequency pulses into a radiofrequency absorbing medium to generate ultrasound pulses or waves directed into the target tissue and wherein all of the pulses are in the range from about 1 femtosecond to about 1 microsecond.

18. The method of claim 12, further comprising:
supplying insulin to the target tissue via:
(d) an insulin patch or an insulin pump under control of the processor.

19. The method of claim 12, further comprising:
transmitting via the processor the current glucose concentration and/or the graph to medical personnel.

20. The method of claim 12, wherein, in the generating, directing, detecting, measuring, and determining steps:
the glucose sensor, the processor, and the feedback unit are integral to form an integral apparatus, or
the glucose sensor is separate from the processor and feedback unit to form a separated apparatus, wherein the sensor is configured to transmit the signal to the processor.

21. The method of claim 20, wherein, in the generating, directing, detecting, measuring, and determining steps:
the integral apparatus comprises:
a wrist watch further comprising an invasive glucose sensor configured to use blood or interstitial fluid to calibrate the noninvasive glucose sensor, or
a pair of glasses, wherein the feedback unit is a head up display associated with the glasses, or
the separated apparatus comprises a contact lens including the noninvasive glucose sensor.

22. The method of claim 21, wherein, in the generating, directing, detecting, measuring, and determining steps, the wrist watch further comprises of a pulse rate monitor, a blood oxygenation monitor, a body temperature monitor, and/or a blood pressure monitor.

23. The method of claim 22, further comprising:
wirelessly communicating pulse rate, blood oxygenation, body temperature, and/or blood pressure with a cell phone, and
displaying a current glucose concentration and a graph of glucose concentration vs. time.

24. The method of claim 23, further comprising:
wirelessly communicating with a health care facility or a non-health care facility.

* * * * *